United States Patent
Leonhardt et al.

(10) Patent No.: US 10,646,644 B2
(45) Date of Patent: May 12, 2020

(54) STIMULATOR, PUMP AND COMPOSITION

(71) Applicant: CalXStars Business Accelerator, Inc., Santa Monica, CA (US)

(72) Inventors: Howard J. Leonhardt, Salt Lake City, UT (US); Jorge Genovese, Buenos Aires (AR)

(73) Assignee: CalXStars Business Accelerator, Inc., Santa Monica, CA (US)

( * ) Notice: Subject to any disclaimer, the term of this patent is extended or adjusted under 35 U.S.C. 154(b) by 0 days.

(21) Appl. No.: 15/460,129

(22) Filed: Mar. 15, 2017

(65) Prior Publication Data

US 2017/0266371 A1   Sep. 21, 2017

Related U.S. Application Data

(60) Provisional application No. 62/454,521, filed on Feb. 3, 2017, provisional application No. 62/385,124, filed
(Continued)

(51) Int. Cl.

| | |
|---|---|
| *A61M 5/142* | (2006.01) |
| *A61N 1/372* | (2006.01) |
| *A61M 39/02* | (2006.01) |
| *A61N 1/32* | (2006.01) |
| *A61M 39/00* | (2006.01) |
| *A61N 1/375* | (2006.01) |

(Continued)

(52) U.S. Cl.
CPC .... *A61M 5/14276* (2013.01); *A61M 39/0208* (2013.01); *A61N 1/326* (2013.01); *A61N 1/37205* (2013.01); *A61M 2039/0036* (2013.01); *A61N 1/36002* (2017.08); *A61N 1/3629* (2017.08); *A61N 1/375* (2013.01)

(58) Field of Classification Search
CPC .......... A61M 5/14276; A61M 39/0208; A61M 2039/0036; A61N 1/37205; A61N 1/326; A61N 1/375; A61N 1/36002; A61N 1/3629
See application file for complete search history.

(56) References Cited

U.S. PATENT DOCUMENTS

| | | | |
|---|---|---|---|
| 5,543,318 A | 8/1996 | Smith et al. | |
| 5,693,029 A | 12/1997 | Leonhardt et al. | |

(Continued)

FOREIGN PATENT DOCUMENTS

| | | |
|---|---|---|
| CA | 2685161 A1 | 10/2007 |
| EP | 0603451 A1 | 6/1994 |

(Continued)

OTHER PUBLICATIONS https://www.dicardiology.com/content/bioleonhardt-unveils-stem-pump Jan. 28, 2014.*

(Continued)

*Primary Examiner* — Mark Bockelman
(74) *Attorney, Agent, or Firm* — TraskBritt

(57) ABSTRACT

Described is a low voltage, pulsed electrical stimulation device for controlling expression of, for example, follistatin, a muscle formation promotion protein, by tissues. Epicardial stimulation is especially useful for heart treatment. Follistatin controlled release is also useful for treating other ailments, such as erectile dysfunction, aortic aneurysm, and failing heart valves.

14 Claims, 3 Drawing Sheets

Related U.S. Application Data on Sep. 8, 2016, provisional application No. 62/375,271, filed on Aug. 15, 2016, provisional application No. 62/364,472, filed on Jul. 20, 2016, provisional application No. 62/363,012, filed on Jul. 15, 2016, provisional application No. 62/352,930, filed on Jun. 21, 2016, provisional application No. 62/308,702, filed on Mar. 15, 2016.

(51) Int. Cl.
  *A61N 1/36* (2006.01)
  *A61N 1/362* (2006.01)

(56) References Cited

U.S. PATENT DOCUMENTS

| | | | |
|---|---|---|---|
| 5,713,917 | A | 2/1998 | Leonhardt |
| 5,725,377 | A | 3/1998 | Lemler et al. |
| 6,344,052 | B1 | 2/2002 | Greenan et al. |
| 6,988,004 | B2 | 1/2006 | Kanno et al. |
| 7,341,062 | B2 | 3/2008 | Chachques et al. |
| 7,483,749 | B2 * | 1/2009 | Leonhardt ............ A61N 1/326 607/50 |
| 7,686,799 | B2 * | 3/2010 | Leonhardt ......... A61M 25/0068 600/7 |
| 7,881,784 | B2 | 2/2011 | Pasricha |
| 8,133,267 | B2 | 3/2012 | Leonhardt et al. |
| 8,639,361 | B2 | 1/2014 | Nathanson |
| 8,660,669 | B2 | 2/2014 | Nemeh et al. |
| 8,738,144 | B2 | 5/2014 | Schneider |
| 8,909,346 | B2 | 12/2014 | Chalmers |
| 8,945,104 | B2 | 2/2015 | Boone et al. |
| 9,032,964 | B2 | 5/2015 | Schuler et al. |
| 9,533,170 | B2 | 1/2017 | Dye et al. |
| 9,656,096 | B2 | 5/2017 | Pilla |
| 2003/0032998 | A1 * | 2/2003 | Altman ............ A61M 25/0084 607/120 |
| 2003/0220556 | A1 | 11/2003 | Porat et al. |
| 2004/0010231 | A1 | 1/2004 | Leonhardt et al. |
| 2004/0115587 | A1 | 6/2004 | Breining et al. |
| 2004/0147906 | A1 | 7/2004 | Voyiazis et al. |
| 2005/0171578 | A1 | 8/2005 | Leonhardt |
| 2006/0030908 | A1 | 2/2006 | Powell et al. |
| 2007/0190028 | A1 | 8/2007 | Qu et al. |
| 2010/0082027 | A1 | 4/2010 | Chalmers |
| 2010/0184183 | A1 | 7/2010 | Schussler et al. |
| 2012/0156648 | A1 | 6/2012 | Kaufman et al. |
| 2013/0253413 | A1 | 9/2013 | Levine et al. |
| 2014/0023983 | A1 | 1/2014 | Lowe et al. |
| 2017/0028184 | A1 | 2/2017 | Godden et al. |
| 2017/0266371 | A1 | 9/2017 | Leonhardt et al. |
| 2017/0274206 | A1 | 9/2017 | Leonhardt |
| 2018/0064935 | A1 | 3/2018 | Leonhardt |

FOREIGN PATENT DOCUMENTS

| | | |
|---|---|---|
| WO | 2006/116728 A2 | 11/2006 |
| WO | 2008/145724 A1 | 12/2008 |
| WO | 2008145724 A1 | 12/2008 |

OTHER PUBLICATIONS

Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
Walsh & Choi "Biology of the RANKL-RANK-OPG System in Immunity, Bone, and Beyond", Front Immunol. 2014; 5: 511.
Thattaliyath et al., "Modified Skeletal Myoblast Therapy for Cardiac Failure Using AAV SDF1", Proc. Intl. Soc. Mag. Reson. Med. 16, p. 579 (2008).
Prochazka et al., "Cocktail of Factors from Fat-derived Stem Cells Shows Promise for Critical Limb Ischemia" http://www.sciencenewsline.com/news/2016012204520017.html (Jan. 21, 2016).
Wei et al., "Epicardial FSTL1 reconstitution regenerates the adult mammalian heart," Nature 525: 479-485 (Sep. 24, 2015).
Hearts build new muscle with this simple protein patch, jacobsschool.ucsd.edu/news/news_releases/release.sfe?d=1813 (Sep. 16, 2015).
Stenn et al., "Bioengineering the Hair Follicle," Organogenesis, 3(1): 6-13 (Jan.-Mar. 2007).
Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).
Control of Hair Growth by a Growth Factor Protein, http://www.hairloss-reversible.com/control-of-hair-growth-by-a-growth-factor-protein/.
Hair Growth Factors, Nanogen, http://www.svijet-kose.com/dokumenti/Serum-vegf.pdf.
Elastatropin® in Scalp & Hair Conditioning https://www.proteingenomics.com/haircare.html.
What Is Elastin? http://www.keracyte.com/index.php/site/page?view=whatIsElastin.
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
Reversing Age-Related Hair Loss and Restoring Healthy Hair Growth in Men and Women https://nutritionreview.org/2015/08/reversing-age-related-hair-loss-and-restoring-healthy-hair-growth-in-men-and-women/ (Aug. 24, 2015).
Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4(3):312-5 (Dec. 1999).
Interesting study about prolactin, VEGF and angiogenic inhibition, http://www.regrowth.com/hair-loss-forums/topic/interesting-study-about-prolactin-vegf-and-angiogenic-inhibition/ (Nov. 2006).
Medtronic "Cardiac Resynchronization Therapy (CRT) Devices for Heart Failure" http://www.medtronic.com/us-en/patients/treatments-therapies/crt-devices.html.
Columbia "Implant Procedure Concepts—Pacemaker, ICD and CRT Overview", http://www.columbia.edu/itc/hs/medical/hickey/docs/Pacemaker,%20ICD%20and%20CRT%20Overview%20022007.pdf.
P. Banerjee "Electrical muscle stimulation for chronic heart failure: an alternative tool for exercise training?" Curr Heart Fail Rep., 7(2):52-8. doi: 10.1007/s11897-010-0013-9 (Jun. 2010).
Bio-Leonhardt "Micro Stimulator" http://www.bioleonhardt.com/micro-stimulator/.
Hopkins Medicine, "Overview of Pacemakers and Implantable Cardioverter Defibrillators (ICDs)", http://www.hopkinsmedicine.org/healthlibrary/conditions/cardiovascular_diseases/overview_of_pacemakers_and_implantable_cardioverter_defibrillators_icds_85,P00234/.
Robert Ferris, "Battle against baldness turns to stem cells" http://www.cnbc.com/2015/01/29/studies-indicate-its-possible-to-use-stem-cells-to-cure-baldness.html (Jan. 29, 2015).
Our Approach to Improve Hair Loss by Increasing Hair Growth Factor IGF-1, http://www.jhgc.com.sg/theory/igf-1/index.html.
Sahoo and Losordo, "Exosomes and Cardiac Repair After Myocardial Infarction", Circulation Research, 114:333-344 (Jan. 16, 2014).
Tamaki et al., "Cardiomyocyte Formation by Skeletal Muscle-Derived Multi-Myogenic Stem Cells after Transplantation into Infarcted Myocardium", PLoS ONE 3(3): e1789. doi:10.1371/journal.pone.0001789 (Mar. 2008).
W. Hoffmann, "Regeneration of the gastric mucosa and its glands from stem cells", Curr Med Chem, 15(29):3133-44 (2008).
Yamaguchi, "RANK/RANKL/OPG during orthodontic tooth movement", Orthod Craniofac Res. May 2009; 12(2):113-9. doi: 10.1111/j.1601-6343.2009.01444.x.
Walsh & Choi "Biology of the RANK* RAN* OPG System in Immunity, Bone, and Beyond", Front Immunol. 2014; 5: 511.

(56) References Cited

OTHER PUBLICATIONS

Kim et al., The effects of electrical current from a micro-electrical device on tooth movement, http://e-kjo.org/search.php?where=aview&id=10.4041/kjod.2008.38.5.337& . . . visited Aug. 2, 2017.
Keles et al. "Inhibition of tooth movement by osteoprotegerin vs. pamidronate under conditions of constant orthodontic force", Eur J Oral Sci. Apr. 2007;115(2):131-6.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21 / 220.
Kanzaki et al. "Local OPG gene transfer to periodontal tissue inhibits orthodontic tooth movement." J Dent Res 2004;83:92/ 925.
K. Hart, Katherine A.nn D.D.S., "RANKL and Osteoprotegerin Levels in Response to Orthodontic Forces" (2012). Theses and Dissertations (ETD). Paper 107. http://dx.doi.org/10.21007/etd.cghs.2012.0127.
Dibart et al. "Tissue response during Piezocision-assisted tooth movement: a histological study in rats", Eur J Orthod (2014) 36 (4): 457-464; DOI: https://doi.org/10.1093/ejo/cjt079.
Almpani et al., "Nonsurgical Methods for the Acceleration of the Orthodontic Tooth Movement", Tooth Movement. Fronl Oral Biol., vol. 18, pp. 80-91 (Karger, Basel, CH 2016) (DOI:10.1159/000382048), Published online: Nov. 24, 2015.
Information Disclosure Statement (IDS) Form (SB08) Mailed on Apr. 9, 2018 for U.S. Appl. No. 15/812,760.
Alice Park, "Shrinking Stem Cells Are the Real Reason for Hair Loss" Time, (Feb. 5, 2016).
Almpani et al., "Nonsurgical Methods for the Acceleration of the Orthodontic Tooth Movement", Tooth Movement. Front Oral Biol., vol. 18, pp. 80-91 (Karger, Basel, CH 2016) (DOI:10.1159/000382048), Published online: Nov. 24, 2015.
B. Borgobello, "FDA approves the treatment of brain tumors with electrical fields", New Atlas, http://newatlas.com/treatment-of-brain-tumors-with-electrical-fields/21433/ (Feb. 13, 2012).
Bio-Leonhardt "Micro Stimulator" http://www.bioleonhardt.com/micro-stimulator, visited Mar. 15, 2017.
Blood Vessels Hold Key to Thicker Hair Growth, https://www.sciencedaily.com/releases/2001/02/010215074636.htm (Feb. 2001).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Columbia "Implant Procedure Concepts—Pacemaker, ICD and CRT Overview", http://www.columbia.edu/itc/hs/medical/hickey/docs/Pacemaker,%20ICD%20and%20CRT%20Overview%20022007.pdf, copyright 2007.
Control of pelage hair follicle development and cycling by complex interactions between follistatin and activin, FASEB J (Jan. 2, 2003).
Control of Hair Growth by a Growth Factor Protein, http://www.hairloss-reversible.com/control-of-hair-growth-by-a-growth-factor-protein, visited Mar. 15, 2017.
D. Grad, "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?_r=0 (Nov. 15, 2014).
D'Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
Elastatropin® in Scalp & Hair Conditioning https://www.proteingenomics.com/haircare.html, visited Mar. 15, 2017.
Electric Tumor Treatment Fields, No. 0827 Policy, http://www.aetna.com/cpb/medical/data/800_899/0827.html (Nov. 18, 2016).
Electrical brain stimulation could support stroke recovery https://www.sciencedaily.com/releases/2016/03/160316151108.htm (Mar. 16, 2016).
FDA Approves Algovita Spinal Cord Stimulation System from Greatbatch, http://www.odtmag.com/contents/view_breaking-news/2015-12-02/fda-approves-algovita-spinal-cord-stimulation-system-from-greatbatch (Dec. 2, 2015).
Fukuoka et al., "The Latest Advance in Hair Regeneration Therapy Using Proteins Secreted by Adipose-Derived Stem Cells," The American Journal of Cosmetic Surgery, 29(4):273-282 (2012).
Fukuoka and Suga, "Hair Regeneration Treatment Using Adipose-Derived Stem Cell Conditioned Medium: Follow-up With Trichograms" Eplasty, 15:e10 (Mar. 2015).
Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26(4):671-80.
Hair Growth Factors, Nanogen, http://www.svijet-kose.com/dokumenti/Serum-vegf.pdf, copyright 2010.
R. Hamman "Modulation of RANKL and Osteoprotegerin in Adolescents Using Orthodontic Forces", Masters Thesis, University of Tennessee (2010).
Hearts build new muscle with this simple protein patch, jacobsschool.ucsd.edu/news/news_releases/release.sfe?id=1813 (Sep. 16, 2015).
HN Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Holding et al. "The correlation of RANK, RANKL and TNFa expression with bone loss volume and polyethylene wear debris around hip implants" Biomaterials 27(30):5212-9 • Nov. 2006.
Hopkins Medicine, "Overview of Pacemakers and Implantable Cardioverter Defibrillators (ICDs)", http://www.hopkinsmedicine.org/healthlibrary/conditions/cardiovascular_diseases/overview_of_pacemakers_and_implantable_cardioverter_defibrillators_icds_85,P00234, visited Mar. 15, 2017.
HU Klein, "Vagus Nerve Stimulation: A new approach to reduce heart failure" Cardiology Journal (2010).
Hy et al., "Insulin-like growth factor 1 and hair growth," Dermatol Online J,; 5(2):1 (Nov. 1999).
Interesting study about prolactin, VEGF and angiogenic inhibition, http://www.regrowth.com/hair-loss-forums/topic/interesting-study-about-prolactin-vegf-and-angiogenic-inhibition/ (Nov. 2000).
Involvement of hepatocyte growth factor/scatter factor and Met receptor signaling in hair follicle morphogenesis and cycling, FASEB J Feb. 2000 14:319-332.
Israeli innovation uses nerve stimulation to treat heart failure https://www.israel21c.org/israeli-innovation-uses-nerve-stimulation-to-treat-heart-failure/ (Feb. 11, 2007).
Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.
Jia et al., "Activin B Promotes Initiation and Development of Hair Follicles in Mice" Cells Tissues Organs, 198:318-326 (Feb. 2014).
Kanno et al., Establishment of a Simple and Practical Procedure Applicable to Therapeutic Angiogenesis, Circulation, 1999, pp. 2682-2687, vol. 99.
Kanzaki et al. "Local RANKL gene transfer to the periodontal tissue accelerates orthodontic tooth movement", Gene Therapy, (2006) 13, 678-685.
Kanzaki et al. "Local OPG gene transfer to periodontal tissue inhibits orthodontic tooth movement." J Dent Res 2004;83:920-925.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:210-220.
Kaur et al. "Electrically conductive polymers and composites for biomedical applications", RSC Adv., 2015,5, 37553-37567 DOI: 10.1039/C5RA01851J.
Khan et al. "Accelerating Tooth Movement: What Options We Have?" J Dent Health Oral Disord Ther 2016, 5(7): 00181.

(56) References Cited

OTHER PUBLICATIONS

Li et al., "Exogenous IGF-1 promotes hair growth by stimulating cell proliferation and down regulating TGF-β1 in C57BL/6 mice in vivo" Growth Hormone & IGF Research, vol. 24, Issues 2-3, pp. 89-94 (Apr.-Jun. 2014).
Marie Ellis, "Cure for baldness? Stem cells bring hope" http://www.medicalnewstoday.com/articles/271898.php.
Mass Device "Greatbatch wins FDA PMA for Algovita SCS" http://www.massdevice.com/greatbatch-wins-fda-pma-for-algovita-scs/ (Dec. 1, 2015).
Medtronic "Cardiac Resynchronization Therapy (CRT) Devices for Heart Failure" http://www.medtronic.com/us-en/patients/treatments-therapies/crt-devices.html, visited Mar. 15, 2017.
Otero et al. "Expression and Presence of OPG and RANKL mRNA and Protein in Human Periodontal Ligament with Orthodontic Force", Gene-Regulation-and-Systems-Biology, 2016, 10, 15-20.
Our Approach to Improve Hair Loss by Increasing Hair Growth Factor IGF-1, http://www.jhgc.com.sg/theory/igf-1/index.html, visited Mar. 15, 2017.
Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).
Zhang et al. "Exosomes derived from human embryonic mesenchymal stem cells promote osteochondral regeneration", Osteoarthritis and Cartilage, vol. 24, Issue 12, Dec. 2016, pp. 2135-2140.
Yamakazi et al., "Hair cycle-dependent expression of hepatocyte growth factor (HGF) activator, other proteinases, anc proteinase inhibitors correlates with the expression of HGF in rat hair follicles", J Investig Dermatol Symp Proc., 4(3):312-5 (Dec. 1999).
Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.
Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.
Spadari et al., Electrical stimulation enhances tissue reorganization during orthodontic tooth movement in rats; Clinical Oral Investigations, Jan. 2017, vol. 21, Issue 1, pp. 111-120, Abstract.
Spadari et al., Electrical stimulation enhances tissue reorganization during orthodontic tooth movement in rats; Clinica Oral Investigations, Jan. 2017, vol. 21, Issue 1, pp. 111-120, Abstract.
Signature Orthodontics "Accelerated Tooth Movement", http://www.sigortho.com/accelerated-tooth-movement, visited Mar. 15, 2017.
Seifi & Jeszri "Correlation of bone resorption induced by orthodontic tooth movement and expression of RANKL in rats", Dental Journal, vol. 26, No. 4 (2009).
Schardong et al., "Intradialytic neuromuscular electrical stimulation reduces DNA damage in chronic kidney failure patients: a randomized controlled trial," Biomarkers, vol. 23, Issue 5, 2018, pp. 1-11.
Prochazka et al. "Therapeutic Potential of Adipose-Derived Therapeutic Factor Concentrate for Treating Critical Limb Ischemia," Cell Transplantation, 25(9), pp. 1623-1633(11) (2016).
Nimeri et al. "Acceleration of tooth movement during orthodontic treatment—a frontier in Orthodontics", Prog Orthod 2013; 14:42; DOI: 10.1186/2196-1042-14-42.
Niiranen et al., "Relative Contributions of Arterial Stiffness and Hypertension to Cardiovascular Disease: The Framingham Heart Study," Journal of the American Heart Association, vol. 5, No. 11, 2016, 8 pages.

Mosteiro et al. "Tissue damage and senescence provide critical signals for cellular reprogramming in vivo." Science, 2016; 354 (6315): aaf4445 DOI: 10.1126/science.aaf4445.
Leonhardt's Launchpads Announces Filing of Patent for Bioelectric Stimulation Controlled Klotho Expression—Powerful Anti-aging and Regeneration Promoting Protein, by API PODDER, Published: Mar. 13, 2019, available online at < https://mysocialgoodnews.com/leonhardts-launchpads-announces-filing-of-patent-for-bioelectric-stimulation-controlled-klotho-expression-powerful-anti-aging-and-regeneration-promoting-protein/.
Dong-Hwan Kim et al., The effects of electrical current from a micro-electrical device on tooth movement, Korean Orthod., Oct. 2008, 38(5):337-346.
Chernet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Chang et al. Effect of Pulse-Burst Electromagnetic Field Stimulation on Osteoblast Cell Activities; Bioelectromagnetics 25:457-465 (2004).
Cerrada et al. "Hypoxia-Inducible Factor 1 Alpha Contributes to Cardiac Healing in Mesenchymal Stem Cells-Mediated Cardiac Repair," Stem Cells and Development, 22(3): 501-511 (2013).
Bradshaw et al. "Designer self-assembling hydrogel scaffolds can impact skin cell proliferation and migration" Nature Scientific Reports, vol. 4, Article No. 6903 (2014).
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.0rg/10.1155/2013/105873.
Abstract of Zhang et al., "Comparison of arterial stiffness in non-hypertensive and hypertensive population of various age groups," Jan. 24, 2018, 2 pages.
Abstract of Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages.
Abstract of Collette et al., "Measurement of the local aortic stiffness by a non-invasive bioelectrical impedance technique," in Medical & Biological Engineering, vol. 49, No. 4, Feb. 2011, pp. 431-439, Available online at < https://www.ncbi.nlm.nih.gov/pubmed/21286830 >, 1 page.
Krishnan et al. (eds.), "Biological Mechanisms of Tooth Movement", John Wiley & Sons 2015 (10 pages).
Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).
Shoji-Matsunaga et al. "Osteocyte regulation of orthodontic force-mediated tooth movement via RANKL expression" Scientific Reports, 7: 8753, published online Aug. 18, 2017, DOI:10.1038/s41598-017-09326-7.
Li, et al. "Local injection of RANKL facilitates tooth movement and alveolar bone remodelling." Oral Diseases, 25(2), 550-560. https://doi.org/10.1111/odi.13013.
Lee et al. "Hepatocyte growth factor (HGF) activator expressed in hair follicles is involved in in vitro HGF-dependent hair follicle elongation," J. Dermatol. Sci., 25(2):156-63 (Feb. 2001).

* cited by examiner

STIMULATOR, PUMP AND COMPOSITION

CROSS-REFERENCE TO RELATED APPLICATIONS

This application claims the benefit under 35 USC § 119 of:

U.S. Provisional Patent Application Ser. No. 62/308,702, filed Mar. 15, 2016;

U.S. Provisional Patent Application Ser. No. 62/363,012, filed Jul. 15, 2016;

U.S. Provisional Patent Application Ser. No. 62/364,472, filed Jul. 20, 2016;

U.S. Provisional Patent Application Ser. No. 62/375,271, filed Aug. 15, 2016;

U.S. Provisional Patent Application Ser. No. 62/385,124, filed Sep. 8, 2016; and U.S. Provisional Patent Application Ser. No. 62/454,521, filed Feb. 3, 2017;

the disclosure of which is incorporated herein in its entirety by this reference.

This application claims the benefit under 35 USC § 119 of U.S. Provisional Patent Application Ser. No. 62/352,930, filed Jun. 21, 2016.

FIELD

The application relates generally to the field of medical devices and associated treatments, and more specifically to precise bioelectrical stimulation of a subject's tissue, augmented with the administration of a composition comprising, among other things, stem cells and nutrients, useful to stimulate and treat the subject, the subject's tissue(s), the subject's organ(s), and/or the subject's cells.

BACKGROUND

Various organs of the body lose, e.g., muscle function due to aging, disease, low blood flow, injury or blood vessel blockage(s). For example, the heart can become subject to heart failure. Realizing this, attempts have been made to address the issue with, e.g., electrical stimulation. For example, U.S. Pat. No. 7,483,749 to Leonhardt et al. (Jan. 27, 2009), the contents of which are incorporated herein by this reference, provided a method for enhancing myogenesis in a subject's injured myocardium, which method comprised identifying an injury or degeneration site in the myocardium and applying electrical stimulation to the site to enhance myogenesis. The method could be used in combination with implantation of myogenic cells into the myocardium, and the electrical stimulation could be applied before or after the implantation of myogenic cells. While good for its time, the method could be improved upon.

Prior art devices either did not produce follistatin at all or were of very high voltages (10 to 40V), which could lead to electrical disturbances in the heart tissue and which could be painful in use for applications such as treating erectile dysfunction.

BRIEF SUMMARY

Described is an organ regeneration stimulator pump and composition system.

Also included is bioelectric stimulator programmed to activate release in the subject of SDF1, IGF1, EGF, HGF, PDGF, eNOS, VEGF, Activin A+B, RANKL/OPG/TNF A, Follistatin, and Tropoelastin.

A preferred such system includes:

1. A bioelectric stimulator that controls/stimulates release/production of SDF1, IGF1, EGF, HGF, PDGF, eNOS, VEGF, Activin A+B, RANKL/OPG/TNF A, Follistatin and Tropoelastin. In certain embodiments, it also releases/stimulates GDF-10, GDF-11, Relaxin and/or neurogenin-3.

2. A micro infusion pump (e.g., a FluidSync™ micropump available from Fluidsynchrony of Pasadena, Calif. US), which is programmable and re-fillable and preferably with a low cell damage design. Such a pump preferably includes refilling silicon septum ports and reservoir chambers.

3. A multi-component organ regeneration composition that includes (depending on the application) adipose-derived stem cells, muscle-derived stem cells (when needed for muscle), exosomes, Micro RNAs, nutrient hydrogel, growth factor cocktail, organ specific matrix, selected alkaloids, and/or selected anti-inflammatory agents.

The pump and stimulator are associated with (e.g., connected to) the organ to be treated/regenerated with pacing infusion lead (available from Nanoscribe of Eggenstein-Leopoldshafen, Germany). The interface with the organ varies by organ, e.g., a conductive soft wrap can be used for certain applications.

The stimulator can be designed to externally deliver all regeneration promoting signals wirelessly to the subject's organ(s), tissue(s), and/or cells.

In certain embodiments, described is a preferred device for regenerating organs by controlled release of organ regenerating promoting proteins by a bioelectric stimulator. Such a device may utilize bioelectric signals delivered wirelessly to the organ(s), tissue(s), and/or cell(s) being treated. Such a device may utilize bioelectric organ regeneration signals delivered via the nervous system of the subject being treated.

In certain embodiments, described is a device for regenerating organs by controlled release of stem cell homing signals (SDF-1+PDGF), stem cell differentiation signals, blood vessel growth signals, and organ specific tissue building signals In certain embodiments, also described is a device for regenerating organs by controlled release of SDF-1, IGF-1, HGF, EGF, PDGF, eNOS, VEGF, Follistatin, Activin A+B, Relaxin, Tropoelastin, GDF-10, GDF-11 and Neurogenin-3 by bioelectric stimulation.

In certain embodiments, described is a system for regenerating organs, the system comprising: an optional bioelectric stimulator that controls release of organ regeneration promoting proteins; a re-Tillable micro infusion pump; a mixed organ regeneration composition of stem cells and growth factors; and electrical pacing and infusion lead(s) directed to with tip inserted into the organ(s) to be treated. Such a device may include a mixed composition including any or all of the following components: SDF-1, IGF-1, PDGF, Follistatin, Tropoelastin, Relaxin, GDF-10, GDG-11, HGF, EGF, eNOS, VEGF, adipose derived stem cells, iPS cells, cardiac derived stem cells, skeletal muscle derived muscle progenitor cells, endothelial cells, stromal fraction, selected exosomes, selected Micro RNAs, selected alkaloids, selected anti-inflammatory agents, organ specific matrix, and/or nutrient hydrogel.

While not intending to be bound by theory, the following might help to explain the results obtained with the use of the system. Successful organ treatment and/or regeneration has been found to be like good farming. A farmer needs soil pre-preparation, well-designed seeds, sun, irrigation, fertilizers, pruning, and protection against elements and enemies for a good crop. The same is needed for good organ treatment with, e.g., bioelectrical stimulation. The entire ecosystem should be enhanced.

Furthermore, in certain embodiments, only non-invasive bioelectric stimulation controlled protein release first is used before introducing a micro infusion pump or multi-component composition. The pump and composition are best used in severe disease states.

In such embodiments, the scarred organ tissue is first prepared before stem cell recruitment by changing the milieu so that when the stem cells arrive they know what they should become. For example, a bald head is changed to a hair milieu so that when stem cells are recruited with the SDF-1 homing signal to the bald head the stem cells "know" to become hair, not more bald head tissue.

In another such example, post-heart attack scar tissue is changed to a muscle milieu so that when stem cells are recruited with the SDF-1 homing signal to the scar, they "know" to become muscle, not more fibroblasts which make up scar tissue.

As further example, a new blood supply is grown in a previously injured organ tissue and it is loaded up with nutrients so that when the stem cells arrive, they proliferate and thrive in forming the new healthy tissue.

The most important and most difficult to achieve bioelectric signals are the ones that control stem cell differentiation into useful tissue. The bioelectric signals are also the ones that require the most precise control by the micro stimulator. A little bit to the left of right with the signal and you get bone or fat in the heart instead of stem cells differentiating into cardiac muscle tissue. In situations where the milieu change my not be optimal, this is the only way known to get new good organ tissue.

DETAILED DESCRIPTION

Figure 1:
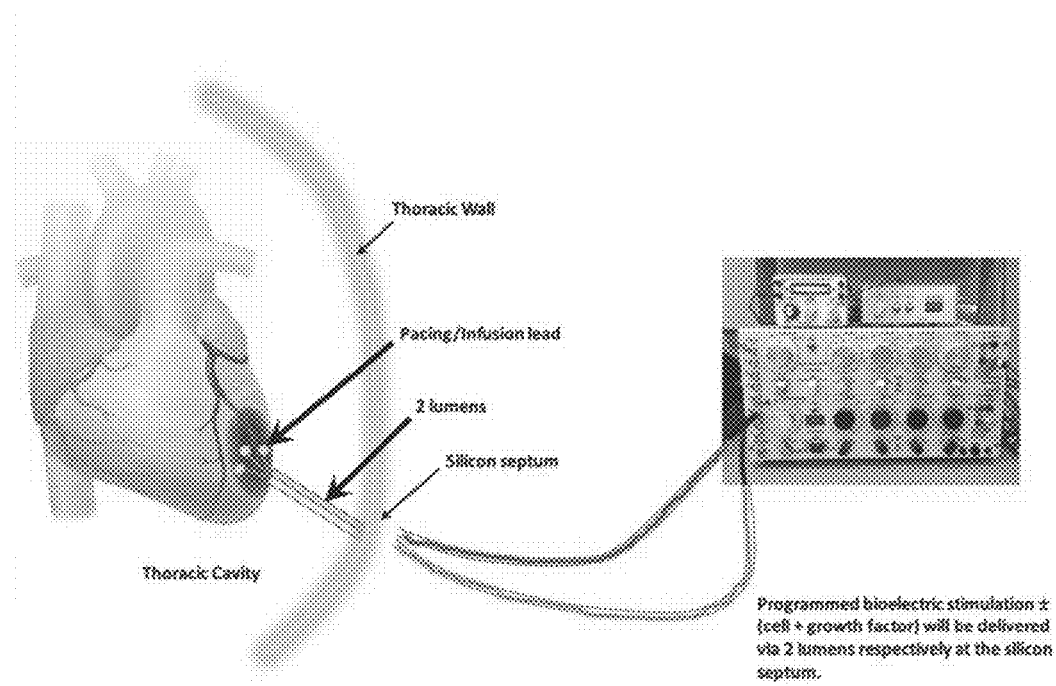
FIG. 1 depicts a programmed bioelectric stimulator (with or without cell and growth factor) for delivery to the heart of a human subject via two lumens respectively at a silicon septum.
Figure 2:
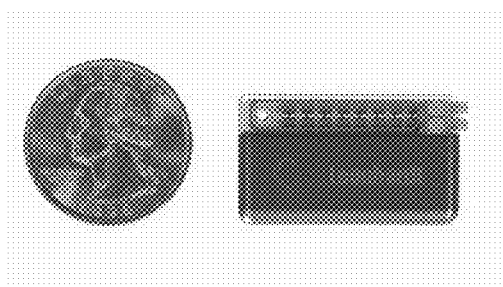
FIG. 2 depicts a programmed bioelectric stimulator depicted alongside a U.S. quarter.
Figure 3:
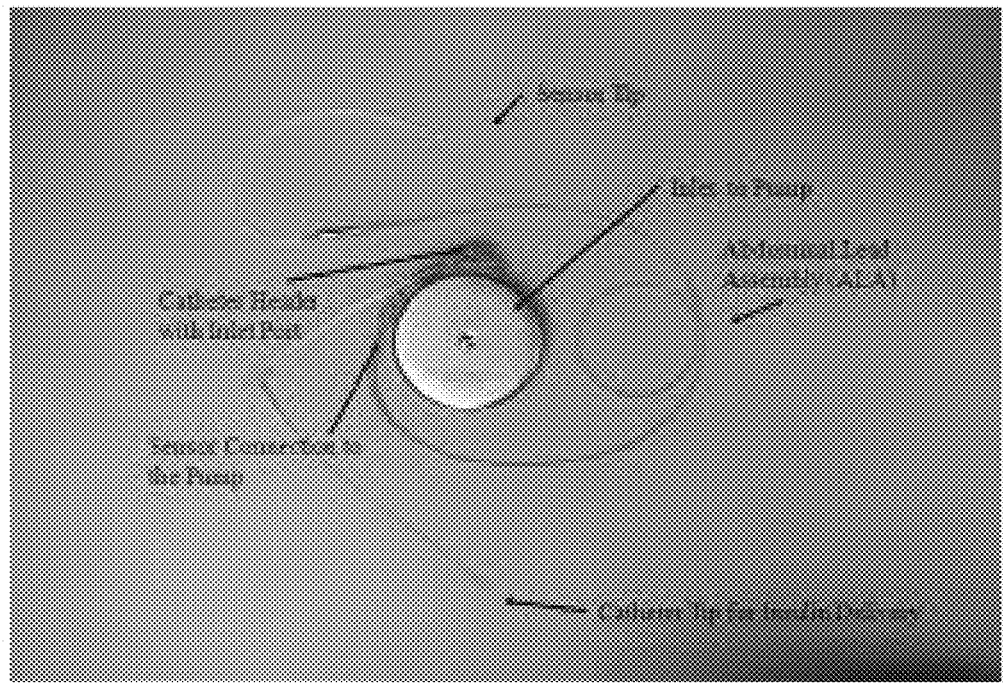
FIG. 3 depicts an interface for use with the system.
Figure 4:
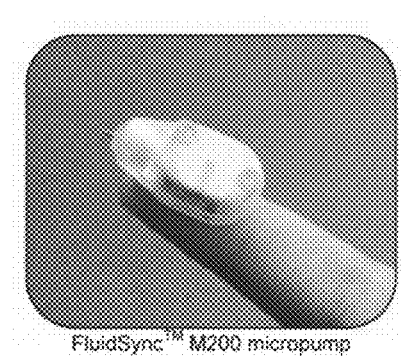
FIG. 4 depicts a micropump for use with the system.
Figure 5:
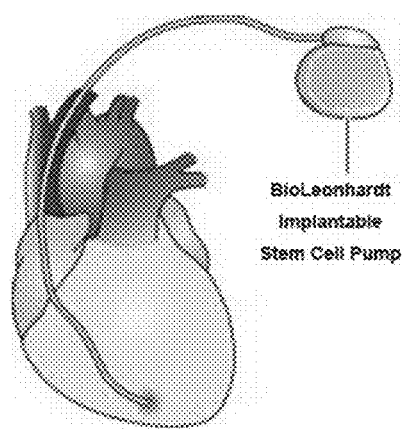
FIG. 5 depicts a pump associated with a subject's heart.

In a preferred embodiment, the organ regeneration composition hereof comprises adipose-derived stem cells, bone marrow-derived stem cells, muscle-derived stem cells (e.g., when needed for muscle), exosomes, MicroRNAs, nutrient hydrogel, growth factor cocktail, organ specific matrix, selected alkaloids, selected anti-inflammatory agents.

The organ specific matrix is a composition comprising cells of an organ which is to be treated. The organ specific matrix is believed to aid in stem cell differentiation, but in any event has been found to be useful in the composition.

It has been found that for the multicomponent composition, cells plus selected growth factors are better than just cells alone. See, e.g., Procházka et al. "Therapeutic Potential of Adipose-Derived Therapeutic Factor Concentrate for Treating Critical Limb Ischemia," Cell Transplantation, 25(9), pp. 1623-1633(11) (2016) and "Cocktail of Factors from Fat-derived Stem Cells Shows Promise for Critical Limb Ischemia," http://wwwsciencenewsline.com/news/2016012204520017.html (Jan. 22, 2016), the contents of each of which are incorporated herein by this reference.

Generally, the system hereof involves a bioelectric stimulator controlling release of SDF-1, IGF-1, HGF, EGF, VEGF, PDGF, eNOS, Follistatin, Activin A+B and Tropoelastin. Optionally and in certain applications, GDF-10, GDF-11, Neurogenin-3 and Relaxin may be included.

In every case in advanced disease states, a micro infusion pump is used for daily delivery of, e.g., 2 ml of organ regeneration composition (comprised of adipose-derived cells or bone marrow-derived mesenchymal stem cells plus cocktail of growth factors (usually derived from amniotic fluid or placenta), selected Micro RNAs, selected alkaloids, selected anti-inflammatory agents, nutrient hydrogel, organ specific matrix, selected exosomes). For muscle regeneration, immature myoblasts are included in the composition.

For heart muscle regeneration, immature myoblasts and cardiac-derived progenitors cells as well as endothelial progenitor cells (EPCs) may be included in the composition.

SDF-1 is generally for recruiting stem cells and maturing blood vessels. IGF-1 is for DNA repair. HGF is for tissue regeneration and reduces arrhythmias in the case of heart. EGF grows tissue. VEGF grows blood vessels. PDGF is a second stem cell homing factor and helps tissue regeneration especially heart. eNOS dilates blood vessels. Follistatin promotes muscle growth. Activin A+B regenerates nerve cells and neurons. Tropoelastin increase elasticity of all tissues especially arteries, skin, heart, aorta. GDF-10 and GDF-11 promote regeneration especially of nerve cells and neurons. Neurogenin-3 is especially helpful in brain and pancreas regeneration. Relaxin helps heart regeneration.

Repeat doses of the composition are also preferred. See, e.g., Gavira et al. "Repeated implantation of skeletal myoblast in a swine model of chronic myocardial infarction," *Eur Heart J*, 31(8): 1013-1021. doi: 10.1093/eurheartj/ehp342 (2010), the contents of which are incorporated herein by this reference.

The micro voltage signal generator may be produced utilizing the same techniques to produce a standard heart pacemaker well known to a person of ordinary skill in the art. An exemplary microvoltage generator is available (for experimental purpose from Cal-X Stars Business Accelerator, Inc. DBA Leonhardt's Launchpads or Leonhardt Vineyards LLC DBA Leonhardt Ventures of Salt Lake City, Utah, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

The construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

Referring now to FIG. 1, depicted is a human use stimulator and pump for use with treatment of, e.g., the heart. Preferably, such a device is about the size of two quarters (available from QIG Greatbatch/Greatbatch, Inc. of Frisco, Tex., US) and is programmable and re-fillable with low cell damage design. Refilling may be by silicon septum ports and reservoir chambers. Depicted particularly in FIG. 1 are the subject's heart, the pacing lead, the infusion lead, the thoracic cavity, two lumens, thoracic wall, silicon septum, and a larger programmed/programmable bioelectric stimulator with composition (e.g., cells and growth factors) for delivery via two lumens via the silica septum. The microinfusion pump for continuous or repeat delivery of a liquid composition, which microinfusion pump includes silicon septum ports and associated reservoir chambers connected to the bioelectric stimulator microinfusion pump to the tissue with a pacing infusion lead.

The pacing infusion lead may be built or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area pitch may be constructed by cutting conduction polymer to shape and forming plastic into a flat bag with outlet ports in strategic locations.

Micro stimulators may be purchased or built in the same manner heart pacemakers have been made since the 1960's. Micro infusion pumps can be purchased or produced similar to how they have been produced for drug, insulin, and pain medication delivery since the 1970's. The programming computer can be standard laptop computer. The programming wand customary to wireless programming wands may be used to program heart pacers.

Any one of the protein expression signals work well on their own for organ regeneration, but they work better together. SDF-1 is the most powerful regeneration protein followed by IGF-1.

Wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

A cork screw tip is of a standard type utilized to secure most heart pacemakers in heart tissue.

Wireless delivery of the signal or electro-acupuncture needle delivery is contemplated.

For human use, it has been determined that longer repeat doses were needed and a natural release from a patient's own electrically stimulated cells would lead to successful human heart regeneration. For example, the described signals for follistatin release match more closely with the natural low voltage signals in the human body.

Additionally, the micro stimulator and micro pump and regeneration composition and bioelectric signaling programming may be used to generate tissue(s) and/or organ(s), such as hair and skin. Alternatively, the system may be used for hair removal.

With respect to hair regeneration, the expression signals for hair regeneration promoting growth factors/proteins are described herein as are the study durations for each signal.

Particularly described are a method and apparatus for producing hair growth stimulation using bioelectric energy, topical compositions, stem cell/growth factor micro infusions and combinations thereof. By using bioelectric signaling resulting from specific protein expressions and their cellular responses to exposure to specific micro voltages. The described system controls release of SDF-1 a stem cell homing factor as well as IGF-1, HGF, EGF, Follistatin, Tropoelastin, eNOS and VEGF as well as micro infusion delivery of an, e.g., 15 component hair regeneration cocktail which includes nutrient hydrogel, thus providing all the supporting element to grow a full head of hair.

A preferred composition includes adipose-derived cells (or bone marrow derived MSCs or any pluripotent stem cell, such as iPS cells) and growth factor mix which should include (SDF-1, IGF-1, EGF, HGF, PDGF, VEGF, eNOS, activin A+B, follistatin, relaxin, GDF-10, GDF-11 and tropoelastin plus selected exosomes (miR-146a, miR-294, mES-Exo) plus selected alkaloids (harmine and tetrahydroharmine) plus selected anti-inflammatory factors plus nutrient hydrogel (IGF-1, SDF-1, HGF plus FGF) plus organ specific matrix. For regenerating muscle one includes into the composition skeletal muscle or cardiac muscle-derived cells. Also, preferably included are amniotic fluid, placenta, or cord blood when available.

Exosomes represent a specific subset of secreted membrane vesicles, which are relatively homogeneous in size (30-100 nm). Exosomes have been proposed to differ from other membrane vesicles by its size, density, and specific composition of lipids, proteins, and nucleic acids, which reflect its endocytic origin Exosomes are formed in endosomal vesicles called multivesicular endosomes (MVEs) or multivesicular bodies, which originate by direct budding of the plasma membrane into early endosomes. The generation of exosomes to form MVEs involves the lateral segregation of cargo at the delimiting membrane of an endosome and inward budding and pinching of vesicles into the endosomal lumen. Because exosomes originate by two successive invaginations from the plasma membrane, its membrane orientation is similar to the plasma membrane. Exosomes from many cell types may contain similar surface proteins as the cell from which it is derived. Membrane proteins that are known to cluster into microdomains at the plasma membrane or at endosomes, such as tetraspanins (CD63, CD81, CD82), often are also enriched in EVs. It is also thought that endosomal sorting complex responsible for transport system and tetraspanins, which are highly enriched in MVEs, play a role in exosome production. How cytosolic constituents are recruited into exosomes is unclear but may involve the association of exosomal membrane proteins with chaperones, such as HSC70, that are found in exosomes from most cell types. MVEs are also sites of miRNA-loaded RNA-induced silencing complex accumulation, and the fact that exosome-like vesicles are considerably enriched in GW182 and AGO2 implicates the functional roles of these proteins in RNA sorting to exosomes. Exosomes are released to the extracellular fluid by fusion of MVE to the plasma membrane of a cell, resulting in bursts of exosome secretion. Several Rab GTPases such as Rab 27a and Rab27b, Rab11 and Rab35, all seem to be involved in exosomes release.

In some cases, SDF-1 recruits via a presumed homing signal new reparative stem cells. to the damaged organ. VEGF causes new nutrient and oxygen producing blood vessels to grow into the area being treated. IGF-1 repairs damaged cells, tissues and organs. follistatin repairs damaged muscle. tropoelastin adds elasticity to treated tissues making them more compliant. Hepatocyte growth factor aides in all repair processes and in the specific case. of the heart regeneration reduces the risk of arrhythmias. All of these proteins work together to fully regenerate an organ over time.

The healing process can be accelerated with the use of a micro infusion pump that is filled with various types of stem cells and growth factors and in some cases drugs.

In certain embodiments, described is a method of inhibiting the growth of cancer cells in a target region, wherein the method includes treating the cancer cells with an anti-cancer drug; and applying an electric field to the target region for a period of time, wherein the electric field has frequency and field strength characteristics selected to inhibit the growth of cancer cells in the target region. In such a method, in the applying step, the field may be applied in at least two different directions in an alternating sequence.

In such a method, the drug dosage may be less than 20% of a standard dosage for the drug.

In such a method, the period of time is typically at least 24 hours.

In such a method, the field strength is typically at least 1 V/cm.

In such a method, the drug typically comprises at least one of paclitaxel, doxorubicin cyclophosphamide, and cisplatin. In such a method, the field strength is typically at least 1 V/cm and the period of time is at least 24 hours.

Also described in certain embodiments is a method of killing or inhibiting the growth of cancer cells in a target region, wherein the method includes applying an electric field to the target region for a period of time while the cancer cells are being treated with an anti-cancer drug, wherein the electric field has a field strength in the target region of at least 1 V/cm.

In such a method, the drug dosage is less than 20% of a standard dosage for the drug.

In such a method, the period of time is at least 24 hours.

In such a method, the drug comprises at least one of paclitaxel, doxorubicin cyclophosphamide, and cisplatin.

In such a method, the field strength is between 1 V/cm and 5 V/cm and the period of time is at least 24 hours.

In such a method, in the applying step, the field is applied in at least two different directions in an alternating sequence. Typically, the drug comprises cyclophosphamide, and typically, the period of time is at least 6 hours.

The described system is currently being investigated for various applications including heart and cardiovascular (e.g., heart regeneration, aorta regeneration, biological pacemaker regeneration, heart valve regeneration, artery regeneration, limb blood flow improvement and limb salvage, and wireless diabetic foot ulcer treatment), brain (e.g., brain regeneration, stroke, concussion, Parkinson's, Alzheimer's, memory and cognitive function improvement, cerebral aneurysm treatment and cancer, and cognitive function improvement), cosmetic & personal care (e.g., breast regeneration, dental gum regeneration and tooth pulp storage, orthodontics, skin regeneration, erectile dysfunction treatment, and hair regeneration), major organ regeneration (e.g., eye, pancreas regeneration, lung, liver regeneration, kidney regeneration, ear hearing, bladder regeneration, whole body regeneration, and sub-gastric mucosa), and associated cancer treatment (e.g., some organ specific technology platforms have integrated cancer tumor stoppage signals).

The described system may be incorporated into, for example, a whole body regeneration chamber that analyzes the body for its deficiencies and precisely delivers the right stem cells and proteins to the right location at the right time combined with programmed infusion of whole body regeneration substances. Ultimately, the goal for the technology is whole and complete body regeneration, every organ.

What follows are preferred signals. For example, described are two PDGF expression control signals. One low voltage and one higher voltage. Test tissue=sheep heart tissue. Test cells=mesenchymal stem cells.

30% PDGF increase with 3 V/cm, 10 Hz, 2 μA (0.000002 amps) and pulse duration of 0.2 ms.

230% PDGF increase with 20 V/cm 100 Hz, 0.25 μA (2.5e-7 amps) and pulse duration of 40 pulses/s, width of 100 μs.

40 minute treatment cycles 2 times a week for 4 weeks and then 3 times a week for 12 weeks.

VEGF—Blood vessel sprouting growth=0.1V applied at a frequency of 50 Hz. Duration 3 minutes.

SDF-1—Stem cell recruiting signal (Leonhardt I Signal)=30 pulses per second with a voltage of 3.5 mV, and successively alternating currents of 700 to 1500 picoamps for one minute, and again with 700 to 1500 picoamps for one minute+stimulated with current of 0.25 mA, pulse duration of 40 pulses/s, pulse width of 100 μs, and frequency of 100 Hz—each signal for 40 minutes to 8 hours a day for 2 to 36 months as needed for ideal results. Duration 7 minutes.

Stem cell proliferation signals—15 mV and a current of 500 picoamps at 70 pulses per minute for 3 hours plus 20 pulses per minute, a pulse amplitude of from 2.5-6 volts, and a pulse width of from 0.2-0.7 milliseconds for 3 hours. Duration 3 minutes.

Stem cell differentiation signals to become muscle (Leonhardt Signals)—200 picoamps for 10 seconds for 1 hour+the pulse has an amplitude of 5 volts and a width of 0.5 milliseconds for 1 hour. Duration 1 minute.

Follistatin—(muscle growth) production signal (Genovese+Leonhardt)—10V @ 50 HZ and 100 HZ 0.25 mA (working on lower voltage signal). Duration 1 minute.

HGF—epatocyte growth factor (arrhythmia reduction) signal (Genovese+Leonhardt)—3.5V stimulation in 10 second bursts, 1 burst every 30 seconds @ frequency 50 HZ. Duration 5 minutes.

IGF-1 3 mV with electric frequency of 22 Hz, and electric current of 1 mA for 15 minutes and 3 mA for 15 minutes. Duration 5 minutes.

Tropoelastin—0.06 V with 50 Hz alternating electrical field and electric current of 1 mA for 15 minutes and 3 mA for 15 minutes. Duration 2 minutes.

RANKL/TNF Alpha nuclear factor-kappa B (NF-κB) ligand/TNF Alpha—3 MV at 2/100 Hz alternating frequency with current of 3 mA followed by 15 Hz, I Gauss EM field, consisting of 5-millisecond bursts with 5 microsecond pulses followed by 200-μs pulse duration at 30 Hz and with current amplitude of 140 mA.

>Optional use depending on application.

eNOS—Alternating high-frequency (HF) and medium-frequency signals (MF)—Symmetric, biphasic, trapezoid pulses, with 400-μs pulse duration and 1.5/1-s ramp-up/ramp-down duration, respectively. HF consisted of 75 Hz pulses with 6 s on-21 s off for 15 minutes. MF consisted of 45 Hz pulses with 5 s on-12 s off for 15 minutes. Followed by stimulation duration set as 20 min for both 1 Hz and 20 Hz stimulations. For 1 Hz stimulation, stimulation was applied for 9 sec, followed by a 1 sec silent period, a total of 1080 stimulations for 20 min. For 20 Hz stimulation, stimulation was applied for 2 sec, followed by silent period for 28 sec, a total of 1600 stimulations for 20 min. Duration 2 minutes.

Activin B—6 mv at 150 HZ Monophasic square wave pulse 0.1 ms in duration current of 15 mA for 15 minutes. Duration 2 minutes.

EGF—10 V/cm, pulse-width 180 μs, 500 Hz. Duration 9 minutes.

An exemplary bioelectric signal sequence suggested for heart regeneration in humans split into six phases is as follows.

Phase I—Prepare Scar ("soil prep")—10 minutes
IGF-1 signal 3 minutes
PDGF signal 3 minutes
HGF signal 2 minutes
EGF signal 2 minutes Phase II—Grow New Blood Vessels ("lay irrigation system")—5 minutes
  VEGF signal—3 minutes
  SDF-1 signal—1 minute
  eNOS signal—1 minute
Phase III—Recruit and Inject Stem Cells ("plant")—15 minutes
  SDF-1 signal—10 minutes
  PDGF-1 signal 5 minutes
Phase IV—Build Tissue ("grow")—25 minutes
  Stem Cell Proliferation Signal—5 minutes
  Stem Cell Differentiation Signal—5 minutes
  Follistatin Signal—5 minutes
  Tropoelastin Signal—5 minutes
  GDF-10—2 minutes
  GDF-11—3 minutes
Phase V—Post Tissue Growth Maintenance ("fertilize")—30 minutes
  VEGF—3 minutes
  EGF—2 minutes
  eNOS—2 minutes
  HGF—5 minutes
  PDGF-3 minutes
  Tropoelastin—5 minutes
  Relaxin—5 minutes
  Follistatin—5 minutes
Phase VI—Protect Against Enemies ("pesticides")—10 minutes
  Activin A+B—5 minutes
  IGF-1-5 minutes The invention is further described with the aid of the following illustrative Examples.

EXAMPLES

Example—Controlling Expression of Follistatin

Low voltage pulsed electrical stimulation device for controlling expression of follistatin, a muscle formation promotion protein, from tissues.

Epicardial stimulation is especially useful for heart regeneration.

In one embodiment, the system stimulates the controlled production/release of follistatin, a known myostatin inhibitor, thus promoting the formation of new muscle and repair of damaged or weakened muscle including heart muscle post heart attack. Follistatin-like 1 (FSTL1) is a protein that encourages the growth of healthy cells, contractile muscle tissue and even blood vessels, helping supply the newly created muscle tissue with oxygen and nutrients. This therapy invention was originally designed to reduce or eliminate scarring of the heart following a heart attack and reversing heart failure but may also be applicable to treating other organs suffering of muscle loss or degradation.

The electrical stimulation device promotes the controlled release of follistatin with practical, safe, low voltages.

No other electrical stimulation device promotes the controlled release of follistatin with practical, safe, low voltages. Most prior art devices failed to have the right signal to produce reliably under control follistatin release. Those that did were at dangerous and painful high voltages impractical for use in an implantable device.

The described system produces follistatin under precise dosing control at safe and comfortable low voltages.

The version of the system discussed for this Example includes the following components: Micro voltage signal generator (micro-stimulator from QIG Greatbatch); Pacing and infusion lead; Corkscrew tip; Conductive polymer bandage wrap or patch; Signal programmer; and External battery charging wand.

Relationship Between the Components:

The micro voltage signal generator is attached to the pacing infusion lead with a cork screw tip or conductive polymer bandage or patch to the tissue or organ to be treated. An external signal programmer may be used to program the micro voltage signal generator with the proper signals for treatment including the follistatin producing signal. The device battery may be re-chargeable with an external battery charging wand.

In use, the signal generator sends a signal to the target tissue organ that causes the genes within the DNA of that tissue to start the follistatin synthesis process on demand. The signal generator sends a signal to the target tissue organ that causes the genes within the DNA of that tissue to start releasing follistatin on demand. The follistatin—(muscle growth) production signal ("Genovese+Leonhardt") is preferably 10V @ 50 HZ and 100 HZ 0.25 mA alternating back and forth. A 3V signal is being developed.

The system not only controls the DNA to build ribosomes and proteins, but also controls the gates of the cell membranes opening and closing correctly to promote regeneration.

The essential elements are the micro voltage signal generator and the means for delivering the signal to the target tissue.

A micro infusion pump is included to the system for delivering other supportive substances or even follistatin in greater volume more quickly.

The signal generator may be external or internal. The transmission of the signal may be wireless, via liquid and/or via wires.

The tissue contact interface may be a patch or bandage or may be via electrodes or leads.

The described system produces follistatin under precise dosing control at safe and comfortable low voltages.

The signal generator programmed with the follistatin release signal is directed via a lead, bandage of patch to the target organ tissue in need of muscle repair or build up. As the signal is in stimulation mode the tissue releases follistatin and muscle is built or repaired as needed until full function resumes or the desired enhanced function is reached.

Example—Follistatin Controlled Release is Also Useful for Treating Other Ailments Such as Erectile Dysfunction, Aortic Aneurysms, and Failing Heart Valves Additionally: May be used for erectile dysfunction. Also, it can assist in heart regeneration, erectile dysfunction repair, Peyronie's disease, sport trauma, aortic aneurysm repair, heart valve repair, artery repair, diabetic foot ulcer repair, and as a muscle building product.

Example—Treatment of the Pancreas with Bioelectric Controlled Protein

Treatment of the pancreas with bioelectric controlled protein expression and micro infusion pump stem cell composition delivery A pancreas regeneration system includes three primary components. First, the micro bioelectric regeneration stimulator (micro-stimulator from QIG Greatbatch) that controls release of 10 regeneration promoting proteins including SDF-1 a stem cell homing signal, IGF-1, HGF, EGF, activin A+B, eNOS, VEGF, follistatin and tropoelastin. Second, a programmable, re-fillable micro infusion pump. Third, a fifteen component stem cell-based regeneration composition comprising a variety of cell types, growth factors, BMP-7, PDLI-1, HGH, selected alkaloids, micro RNAs, nutrient hydrogel, NADA and pancreatic matrix.

In use, the stimulator and pump are implanted just below the subject's skin with a re-fillable silicone septum port with pacing infusion lead directed to the pancreas with a total conductive infusion wrap tip that is gentle on the pancreatic tissue. One portion of the pacing infusion lead is directed to the interior portion of the pancreas.

Example

A device for decalcifying and regenerating a heart valves so a patient may keep their own valve(s) rather than receiving an implant. A device for decalcifying and regenerating heart valves so a patient may keep their own instead of getting an implant. The device combines three methods of decalcification. The system regenerates heart valve tissue. Shape reform is combined via a nitinol ring with decalcification and regeneration.

Heart valves become dysfunctional from calcification build up, and clots form, which causes strokes, heart valves lose shape and thus function. Heart valve leaflets degenerate and do not function properly.

Other devices failed to completely de-calcify heart valve and left dangerous deposits. They failed to even attempt to regenerate heart valve tissues. They failed to combine shape reform with decalcification and regeneration, The described system has three methods of decalcification combined, We have the first system for heart valve tissue regeneration. We have the first device and method combining shape reform via a nitinol ring with decalcification and regeneration.

As stated above, heart valves become dysfunctional from calcification build up, clots form which causes strokes, heart valves lose shape and thus function. Heart valve leaflets degenerate and do not function properly.

The device decalcifies the heart valves, restores shape, and regenerates them restoring full normal function.

The disclosed system reduces calcification in a heart valve. It also regenerates the heart valve with stem cell recruitment and differentiation supported by a full range of regeneration promotion proteins. The system may be combined with a non-surgical reforming option when required or thought desirable.

The prior art is believed to have utilized only a single method for decalcification, which was incomplete. No other device has even attempted to regenerate heart valves. Shape reforming devices failed to be combined with decalcification and regeneration essential for full heart valve function recovery.

The disclosed system combines three methods of decalcification, which leads to heart valve tissue regeneration. The system combines shape reform via a nitinol ring with decalcification and regeneration.

Also, it can produce heart valve decalcification system, a heart valve regeneration system, a heart valve shape reform system, a heart varve autologous cell created leaflets, and a heart valve catheter based delivery system.

The version of the system discussed for this Example includes the following components: 1. Abrasive surface burr on tip of catheter for decalcification; 2. Ultrasonic cleaning on tip of catheter; 3. Biological safe solvent cleaner delivery system on tip of catheter; 4. Bioelectric signal delivery array on tip of catheter; 5. Bioelectric SDF·1 stem cell homing signal; 6. Bioelectric IGF-1 DNA repair signal; 7. Bioelectric HGF regeneration signal; 8. Bioelectric EGF regeneration signal; 9. Bioelectric Activin A+B regeneration signals; 10. Bioelectric follistatin regeneration signal; 11. Bioelectric Tropoelastin elasticity regeneration signal; 12. Bioelectric eNOS blood flow signal; 13. Bioelectric VEGF blood flow signal; 14. Bioelectric stem cell proliferation signal; 15. Bioelectric stem cell differentiation control signal; 16. Nitinol ring placement catheter for shape reform; 17. Autologous cell-created heart valve leaflets; 18, Autologous cell-created heart valve placement device; 19. Optical viewing catheter; 20. Cerebral protection device to stop debris from reaching brain; 21. Bioelectric stimulator signal generator; 22. Micro Infusion pump; 23. Suction cup system for holding heart valve leaflet; and 24, Suction system to vacuum away debris.

Relationship Between the Components:

Items 1, 2, and 3 In sequence work to fully decalcify clean the heart valve leaflets and orifice. Item 19 optical viewing systems provide visualization of areas being cleaned. Item 23 the suction cup system helps hold the heart valve leaflets during cleaning. Item 24 suction vacuum helps remove debris. Item 19 provides cerebral protection with a filter or deflector or items 4 to 15 bioelectric regeneration signals powered by item 21 the bioelectric signal generator which is external work to regenerate the native heart valve by recruiting stem cells and building new healthy tissues. Item 16 a nitinol ring is placed by a catheter delivery system only if the above decalcification and regeneration procedure has not restored full function. Item 17 autologous cell created heart valve leaflets are only placed via Item 18 a heart valve catheter-based delivery system if all the previous steps have not restored full function.

The three decalcification catheters; abrasive burr, ultrasonic cleaning and biological safe solvent under high pressure clean the heart valve. The 10 bioelectric regeneration signals regenerate the heart valve. The nitinol ring restores original shape and thus improves function. The autologous cell created heart valve leaflets are placed only if all the decalcification, regeneration, and shape reform steps have failed to restore full normal function. If all of the above has failed a micro infusion pump may be connected to the guiding catheter and a 15. component regeneration cocktail composition may be infused until function is restored.

If the three decalcification steps and 10+ regeneration signals do not restore full heart valve function, then a nitinol ring is placed by catheter in the heart valve orifice to attempt to restore shape and function. If the decalcification, regeneration, and nitinol ring shape reform procedures do not work to restore full function then an autologous cell created heart valve is placed via a catheter delivery system The three cleaning devices are delivered via a deflecting tip guiding catheter to their position. An optical viewing catheter provides visualization. A suction cup holds leaflets. A dental burr is used on tip of deflecting catheter for first cleaning. An ultrasonic cleaner second cleaning. A biological safe solvent high pressure sprayer for third cleaning. The cleaning is followed by regeneration utilizing bioelectric signals delivered via an array on the tip of a catheter that control 10+ protein expressions. If needed a nitinol ring is placed via a catheter to reform shape. If needed a new set of autologous cell created heart valve leaflets are placed via catheter.

The nitinol ring and new heart valve leaflets are only necessary if the decalcification and regeneration procedure failed to restore full normal function. The micro infusion pump is optional.

The heart valve function may be restored with cleaning only. The regeneration procedure may be used after autologous cell-created implant to improve strength and function. The microinfusion pump could replace or supplement the regeneration stimulator.

The three decalcification procedures are completed first under optical guidance. A cerebral protection device is essential. This is followed by the delivery of 10 regeneration signals via the bioelectric signal array at the tip of the catheter. If full normal function is not restored at this point a nitinol ring may be placed to help reform normal shape. If full function is still not restored after all these steps autologous cell created heart valve leaflets may be placed via catheter.

Additionally: A robot could control the full procedure of cleaning, regeneration, nitinol ring placement and percutaneous autologous cell created valve placement.

Example—Hair Growth Stimulation I

The brain cap is connected to the stimulator and pump and treatment is 40 minutes, 3 times a week for 8 to 36 weeks as needed.

A method and apparatus for producing hair growth stimulation using bioelectrical energy, topical composition(s), stem cell/growth factor micro infusions, and combinations thereof. By using bioelectric signaling resulting from specific protein expressions and their cellular responses to exposure to specific micro voltages. The device controls release of SDF-1 a stem cell homing factor as well as IGF-1, HGF, EGF, follistatin, Tropoelastin, eNOS, and VEGF as well as micro infusion delivery of an, e.g., 15 component hair regeneration cocktail which includes nutrient hydrogel, thus providing all the supporting elements to grow a full head of hair. The composition preferably includes at least EGF and HGF.

Low doses on shaven arms and legs are being tested before moving to higher doses on the head. Safety or the bioelectric stimulation signals in sheep has been studied. The bioelectric stimulation delivery (micro-stimulator from QIG Greatbatch) is combined with a 14 electrode helmet and a hair matrix ointment to ensure the bald areas of the head have the "hair protein" signals so when the SDF-1 bioelectric signal recruits stem cells to the balding areas, those stem cells get the "create hair" signal not the "create skin" signal.

What follows is the signal sequence for the hair regeneration. Note—These are the signals to be reached 3 mm deep in the tissues, not the originating signal. The resistance from the driving signal stimulator to the target tissue needs to be calculated to determine the originating signal in order to reach the below target signals 10 mm to 3 cm deep within the target tissues.

40 minute treatment cycles 2 times a week for 4 weeks and then 3 times a week for 12 weeks.

1. VEGF—Blood vessel sprouting growth=0.1V applied at a frequency of 50 Hz.
   >Duration 3 minutes.
2. SDF-1—Stem cell recruiting signal (Leonhardt I Signal)=30 pulses per second with a voltage of 3.5 mV, and successively alternating currents of 700 to 1500 picoamps for one minute, and again with 700 to 1500 picoamps for one minute+stimulated with current of 0.25 mA, pulse duration of 40 pulses/s, pulse width of 100 μs, and frequency of 100 Hz-each signal for 40 minutes to 8 hours a day for 2 to 36 months as needed for ideal results
   >Duration 7 minutes.
3. Stem cell proliferation signals—15 mV and a current of 500 picoamps at 70 pulses per minute for 3 hours plus 20 pulses per minute, a pulse amplitude of from 2.5-6 volts, and a pulse width of from 0.2-0.7 milliseconds for 3 hours.
   >Duration 3 minutes
4. Stem cell differentiation signals to become muscle (Leonhardt Signals)—200 picoamps for 10 seconds for 1 hour+the pulse has an amplitude of 5 volts and a width of 0.5 milliseconds for 1 hour
   >Duration 1 minute.
5. Follistatin—(muscle growth) production signal (Genovese+Leonhardt)—10V @ 50 HZ and 100 HZ for 12 hours each
   >Duration 1 minute.
6. HGF—Hepatocyte growth factor (arrhythmia reduction) signal (Genovese+Leonhardt)—3.5V stimulation in 10 second bursts, 1 burst every 30 seconds @ frequency 50 HZ
   >Duration 5 minutes.
7. IGF-1 (Genovese+Leonhardt)—3 mv with electric frequency of 22 Hz, and electric current of 1 mA for 15 minutes and 3 ma for 15 minutes
   >Duration 5 minutes.
8. Tropoelastin—0.06 V with 50 Hz alternating electrical field and electric current of 1 mA for 15 minutes and 3 mA for 15 minutes.
   >Duration 2 minutes.
9. eNOS—Alternating high-frequency (HF) and medium-frequency signals (MF)—Symmetric, biphasic, trapezoid pulses, with 400-μs pulse duration and 1.5/1-s ramp-up/ramp-down duration, respectively. HF consisted of 75 Hz pulses with 6 second(s) on-21 second(s) off for 15 minutes. MF consisted of 45 Hz pulses with 5 second(s) on-12 second(s) off for 15 minutes. Followed by stimulation duration set as 20 min for both 1 Hz and 20 Hz stimulations. For 1 Hz stimulation, stimulation was applied for 9 sec, followed by a 1 sec silent period, a total of 1080 stimulations for 20 minutes For 20 Hz stimulation, stimulation was applied for 2 sec, followed by silent period for 28 sec, a total of 1600 stimulations for 20 minutes
   >Duration 2 minutes.
10. Activin B—6 mv at 150 HZ Monophasic square wave pulse 0.1 ms in duration current of 15 mA for 15 minutes.
    >Duration 2 minutes.
11. EGF—10 V/cm, pulse-width 180 μs, 500 Hz
    >Duration 9 minutes.

Drop down resistors may be used in the pacing infusion lead line to adjust down voltages when necessary.

Hair Growth

In a method of stimulating hair growth, the method includes: exposing a hair growth structure to a source of narrow band of bioelectric signals without having applied a drug, cosmeceutical, and/or chromophore to the hair growth structure; and applying a bioelectrical signal controlled protein to promote hair growth by maintaining the exposure of the hair growth structure to the source of narrowband of bioelectric signals for protein expression for a clinically effective duration and at a clinically effective depth to stimulate hair growth without causing skin ablation.

The source of narrowband bioelectric signals may be delivered by, e.g., wireless transmission, electro-acupuncture needles, conductive patches doped with hair growth promoting drugs and proteins, a conduction signal helmet or cap, a metal hair scalp tickler or any combination thereof.

The bioelectric signal may produce vascular endothelial growth factor ("VEGF")—to promote hair growth and blood vessel sprouting growth 0.1 V applied at a frequency of 50 Hz.

The bioelectric signal may produce SDF-1, a stem cell recruiting signal—30 pulses per second with a voltage of 3.5 mV and successively alternating currents of 700 to 1500 picoamps for one minute, and again with 700 to 1500 picoamps for one minute and stimulated with current of 0.25 mA pulse duration of 40 pulses/s, pulse width of 100 AμS, and frequency of 100 Hz.

The bioelectrical signal may produce stem cell proliferation signal—15 mV and a current of 500 picoamps at 70 pulses per minute for three (3) hours and 20 pulses per minute, a pulse amplitude of from 2.5-6 volts, and a pulse width of from 0.2-0.7 milliseconds for 3 hours.

The bioelectric signal may produce stem cell differentiation signals—200 picoamps for 10 seconds for 1 hour and the pulse has an amplitude of 5 volts and a width of 0.5 milliseconds for 1 hour.

The bioelectric signal may produce follistatin, a muscle growth production signal—10V at 50 Hz and at 100 Hz for 12 hours each.

The bioelectric signal may produce Hepatocyte growth factor ("HFG"), arrhythmia reduction signal—3.5V stimulation in 10 second bursts, 1 burst every 30 seconds at frequency 50 Hz.

The bioelectric signal may also produce IGF-1—3 mv with electric frequency of 22 Hz, and electric current of 1 mA for 15 minutes and 3 mA for 15 minutes.

The method bioelectric signal may also produce Tropoelastin—0.06V with 50 Hz alternating electrical field and electric current of 1 ma for 15 minutes and 3 ma for 15 minutes.

The method bioelectric signal may also produce RANKL nuclear factor kappa B (NF-KB) ligand—3 MV at: 2/100 Hz alternating frequency with current of 3 mA followed by 15 Hz, 1 Gauss EM field, consisting of 5-millisecond bursts with 5-microsecond pulses followed by 200 Aμs pulse duration at 30 Hz and with current amplitude of 140 mA.

The bioelectric signal may also produces eNOS—Alternating high frequency (HF) and medium-frequency signals (MF)—Symmetric; biphasic, trapezoid pulses, with 400-Aμs pulse duration and 1.5/l-s ramp-up/ramp-down duration, respectively. HF signals consisted of 75 Hz pulses with 6 second(s) on a and 21 second(s) off for 15 minutes. MF signals consisted of 45 Hz pulses with 5 seconds on and 12 second off for 15 minutes. Followed by stimulation duration set as 20 minutes for both 1 Hz and 20 Hz stimulations.

Example—Hair Growth Stimulation II

Described is a method for stimulating hair growth, the method comprising: exposing a hair growth structure to a source of narrow band of bioelectric signals, without having applied a drug, cosmeceutical, and/or chromophore to the hair growth structure; together with bioelectrical signal controlled protein release to promote hair growth by maintaining the exposure of the hair growth structure to the source of narrowband of bioelectric signals for protein expression for a clinically effective duration and at a clinically effective depth to stimulate hair growth without causing skin ablation.

In such a method, the source of narrowband bioelectric signals may be delivered by, for example, wireless transmission, electro-acupuncture needles, conductive patches doped with hair growth promoting drugs and proteins, a conduction signal helmet or cap, a metal hair scalp tickler, or any combination thereof.

In such a method, the bioelectric signal may be used to produce vascular endothelial growth for factor release VEGF—to promote hair growth and blood vessel sprouting growth 0.1V applied at a frequency of 50 Hz.

In such a method, the bioelectric signal may be used to produce SDF-1 a stem cell recruiting signal of 30 pulses per second with a voltage of 3.5 mV, and successively alternating currents of 700 to 1500 picoamps for one minute, and again with 700 to 1500 picoamps for one minute and stimulated with a current of 0.25 mA, pulse duration of 40 pulses/s, pulse width of 100 μs, and frequency of 100 Hz.

In such a method, the bioelectric signal may be used to produce a stem cell proliferation signal—15 mV and a current of 500 picoamps at 70 pulses per minute for 3 hours plus 20 pulses per minute, a pulse amplitude of from 2.5-6 volts, and a pulse width of from 0.2-0.7 milliseconds for 3 hours.

In such a method, the bioelectric signal may be used to produce—stem cell differentiation signals—(Leonhardt Signals)—200 picoamps for 10 seconds for 1 hour+the pulse has an amplitude of 5 volts and a width of 0.5 milliseconds for 1 hour.

In such a method, the bioelectric signal may be used to produce Follistatin—(muscle growth) production signal (Genovese+Leonhardt)—10V @ 50 HZ and 100 HZ for 12 hours each.

In such a method, the bioelectric signal may be used to produce HGF—Hepatocyte growth factor (arrhythmia reduction) signal (Genovese+Leonhardt)—3.5V stimulation in 10 second bursts, 1 burst every 30 seconds @ frequency 50 HZ In such a method, the bioelectric signal may be used to produce IGF-1 (Genovese+Leonhardt)—3 mv with electric frequency of 22 Hz, and electric current of 1 mA for 15 minutes and 3 ma for 15 minutes.

In such a method, the bioelectric signal may be used to produce tropoelastin with 0.06 V at 50 Hz alternating electrical field and electric current of 1 mA for 15 minutes and 3 mA for 15 minutes.

In such a method, the bioelectric signal may be used to produce RANKL nuclear factor-kappa B (NF-KB) ligand—3 MV at 2/100 Hz alternating frequency with current of 3 ma followed by 15 Hz, 1 Gauss EM field, consisting of 5-millisecond bursts with 5-microsecond pulses followed by 200 μs pulse duration at 30 Hz and with current amplitude of 140 mA.

In such a method, the bioelectric signal may be used to produce eNOS—Alternating high-frequency (HF) and medium-frequency signals (MF)—Symmetric, biphasic, trapezoid pulses, with 400 μs pulse duration and 1.5/l-s ramp-up/ramp-down duration, respectively. IF signals consisted of 75 Hz pulses with 6 seconds on, 21 seconds off for 15 minutes. MF signals at consisted of 45 Hz pulses with 5 seconds on, 12 seconds off for 15 minutes. Followed by stimulation duration set as 20 min for both 1 Hz and 20 Hz stimulations. For 1 Hz stimulation, stimulation is applied.

For 1 Hz stimulation, stimulation was applied for 9 seconds, followed by a 1 second silent period, a total of 1080 stimulations for 20 min. For 20 Hz stimulation, stimulation was applied for 2 sec, followed by silent period for 28 seconds, a total of 1600 stimulations for 20 min.

In such a method, the bioelectric signal may be used to produce Activin A—6 mv at 150 HZ Monophasic square wave pulse 0.1 ms in duration current of 15 mA for 15 minutes.

In such a method, the sequence order is preferably VEGF, eNOS, SDF-1, Proliferation, VEGF, eNOS, HGF, IGF-1, Folli statin, Differentiation, Tropoelastin, Follistatin, IGF-1, HGF, SDF-1 and may be repeated.

In such a method, the bioelectric signal may be used to control expression of FGF.

In such a method, the bioelectric signal may be used to control expression of EGF.

For this Example, the system optimally includes the following components: Brain Electroacupuncture Cap; Micro regeneration stimulator and connecting leads; Micro infusion pump; Bioelectric signal program SDF-1=Stem Cell Homing Factor; Bioelectric signal program IGF-1; Bioelectric signal program HGF; Bioelectric signal program EGF; Bioelectric signal program Follistatin; Bioelectric signal program Tropoelastin; Bioelectric signal program eNOS; Bioelectric signal program VEGF; Bioelectric signal program Activin A+B; Hair regeneration cocktail 15 component composition; Bioelectric signal for cell proliferation; and Bioelectric signal to control differentiation.

The brain electroacupuncture cap is placed onto the head of the patient. The micro regeneration stimulator and connecting leads are connected to the brain electroacupuncture cap. The micro infusion pump is connected to the brain electroacupuncture cap. The Micro stimulator runs through a program releasing, e.g., 10 specific proteins for specific purposes all of which work together for hair regeneration. In severe cases of hair loss, a micro pump is filled with the HC-15 fifteen component hair regeneration cocktail comprising three types of stem cells, growth factors, nutrient hydrogel, scalp matrix, and Micro RNAS as well as known topical solutions for hair regeneration.

The micro hair regeneration stimulator may be used as a standalone. Results are accelerated and enhanced with the addition of the micro infusion pump that is re-filled daily, weekly or monthly.

The brain electroacupuncture cap may be adapted from EEG monitoring caps and electro acupuncture needles. The micro stimulator is obtained from an OEM supplier of heart pacemakers. The software is programmed into the stimulator with a standard programmer. The micro pump is obtained from an OEM supplier that makes pumps for drug infusion.

For this Example, the micro regeneration stimulator is essential. For this Example, the brain electroacupuncture cap is optional. One can use tape electrodes or standard electro acupuncture needles instead or the signals can be transmitted by a wireless light like device. The micro infusion pump is optional for severe cases or for accelerating results.

The brain electroacupuncture cap is connected to the stimulator and pump and treatment is 40 minutes three times a week for 8 to 36 weeks as needed.

Example—Brain and Organ Regeneration Device Based on Bioelectric IGF-1 Stimulation An organ regeneration device that produces controlled release of platelet-derived growth factor by bioelectric stimulation is disclosed. The system provides controlled sustained and repeated release of PDGF via a wire conduction lead or wireless signal delivery and may be combined with a micro infusion pump for maximum results in severe organ failure cases.

A Brain and Organ Regeneration Device based on Bioelectric IGF-1 Stimulation is disclosed. The system directs a lead to exactly the right position with the target organ and stimulates controlled expression of IGF-1 in combination with SDF-1, VEGF, HGH, HGF, Follistatin and tropoelastin in the proper sequence to optimize repair and regeneration.

Damaged aged or cancer stricken organs and tissues are unable to be regenerated back to their original health with current available therapies.

Injections wash away and needle pricks are painful and the entry site is too far away from the organ. Other electrical stimulation devices do not: produce the expression IGF-1 or other combination useful proteins in the most effective sequence.

The disclosed system directs a lead to exactly the right position with the target organ and stimulates controlled expression of IGF-1 in combination with SDF-1, VEGF, HGH, HGF, Follistatin, and tropoelastin in the proper sequence to optimize repair and regeneration.

IGF-1 can transport raw materials to the cells for repair and renovation. IGF-1 promotes raw material transport to the cells. Meanwhile, nucleic acids are helpful in repairing the damage in the DNA, while stimulating ceil division. IGF-1 is able to minimize the DNA and cell stellar damage, but also treat the DNA and the cell. The IGF repair cells and thus tissues and organs, especially when delivered over time in combination with other factors such as SDF-1, VEGF, HGH, HGF, follistatin, and tropoelastin.

Controlled on demand expression of IGF-1 can help repair cells, tissues and organs including brain, muscle, pancreas, lung, skin, kidney and liver.

IGF-1 injections and infusions do not get enough repair material to the target organ or tissue and cause inflammation, which is counterproductive to regeneration. Other electrical stimulation systems fail to express the right regenerative proteins at the right time.

The system directs a lead to exactly the right position with the target organ and stimulates controlled expression of IGF-1 in combination with SDF-1f VEGF, HGH, HGF, Follistatin, and tropoelastin in the proper sequence to optimize repair and regeneration. Also, it can produce hearts, kidneys, livers, lungs, brains, pancreas, lung, skin, knees, and elbows, skin, penis, breasts, aorta, arteries, and limbs.

The version of the system discussed for this Example includes the following components: 1. Bioelectric regeneration stimulator (micro-stimulator from QIG Greatbatch); 2. Signal for causing controlled release of IGF-1—applied 20V at 1 Hz with a frequency of 5 ms for 24 hours; 3. Signal for causing controlled release of SDF-1; 4. Signal for causing controlled release of VEGF; 5. Signal for causing controlled release of Human Growth Hormone; 6; Signal for controlled release of Hepatocyte Growth factor; 7. Signal for controlled release of Follistatin; 8. Signal for controlled release of Tropoelastin; 9. Pacing infusion lead to implant in organ or tissue to be treated; 10. Infusion and electrode wide area patch (optional); 11. Wireless transmitter for all signals listed above (optional); 12. Refillable micro pump (optional); 13. External programmer; and 14. External battery charger.

The regeneration stimulator (1) may be implanted just below the skin of the patient or may be external, especially if the wireless option is chosen. For the implantable model, an infusion conduction lead (9) is directed from the stimulator to the organ or tissue to be repaired. The tip of the lead is lodged into the tissue with a corkscrew or other fixation tip. The regeneration stimulator is programmed by an external programmer (13). The stimulator is programmed to cause release of specific regeneration proteins in a preferred sequence to optimize organ repair starting with VEGF, then SDF-1, then IGF-1, then HGH, then Hepatocyte Growth Factor, then Follistatin, then tropoelastin (2 to 8). The wireless version (11) is applied externally with the signal pointed to the organ to be regenerated. The signal may be constantly calibrated to adjust for fat, skin, and other obstacles between the signal generator and the organ of Interest to be treated. The device may be recharged with an external charger (14). In cases of very widespread organ damage, a wide array infusion and electrode patch (10) may be used to cover the damaged organ area more completely. To accelerate the organ regeneration an implantable, programmable, refillable micro infusion pump may be used to deliver various stem cells, nutrient hydrogels Micro RNA's and growth factors and (in some cases) drugs.

SDF-1 recruits via homing signal new reparative stem cells to the damaged organ, VEGF causes new nutrient and oxygen producing blood vessels to grow into the area being treated. IGF-1 repairs damaged cells, tissues and organs. Follistatin repairs damaged muscle. tropoelastin adds elasticity to treated tissues making them more compliant. Hepatocyte growth factor aides in all repair processes and in the specific case of heart regeneration, reduces the risk of arrhythmias. All of these proteins work together to fully regenerate an organ over time. The process am be accelerated with the use of a micro infusion pump that is filled with various types of stem cells and growth factors and in some cases drugs.

The construction of electric signal generators, and pacemakers, are known to the art and can be obtained from OEM suppliers as well as their accompanying chargers and programmers. What is unique is the programming of specific signals to use specific protein expressions at precisely the right time for optimal organ regeneration. Pacing infusion leads may be purchased from a variety of OEM vendors. An infusion and electrode wide area pitch may be constructed by cutting conduction polymer to shape and forming plastic into a flat bag with outlet ports in strategic locations.

Any one of the protein expression signals work well on their own for organ regeneration, but they work better together. As previously identified herein, SDF-1 is the most powerful regeneration protein followed by IGF-1.

Wireless, single lumen infusion pacing lead or infusion conduction wide array patch may all be used to deliver the regeneration signals and substances to the organ of interest to be treated or they may be used in combination.

The regeneration stimulator lead or wireless signal is directed to the organ to be regenerated and the protein signals are delivered. Again, the most important is SDF-1 which recruits new stem cells to the site and its accompanying reverse polarity signal which triggers differentiation of the recruited stem cells into useful tissues.

The second most important is IGF-1, which is highly potent in cell repair. VE'GF helps grow in blood vessels for feeding the newly created and newly regenerated tissues.

An organ regeneration device that produces controlled release of platelet-derived growth factor ("PDGF") by bioelectric stimulation. Failing organs cannot produce enough PDGF to fully regenerate.

Other devices only provide one time delivery of PDGF, which is insufficient to fully regenerate a failing organ. Infusion systems lose too much therapeutic agent.

The system provided herein provides controlled sustained and repeated delivery of PDGF via a wire conduction lead or wireless signal delivery and may be combined with a micro infusion pump for maximum results in severe organ failure cases.

The bioelectric stimulator reads the needs of an organ and produces release of PDGF in just needed amounts to enhance organ regeneration. Researchers previously conducted organ regeneration studies of one time injection of PDGF with a needle and syringe. This is impractical and will not work for major organ repair.

A one time dose is not enough to fully regenerate an organ. To access the organ with a needle and syringe is very invasive, dangerous and painful. Injected or infused PDGF has a high wash out loss rate.

The system provides controlled sustained and repeated release of PDGF via, e.g., a wire conduction lead or wireless signal delivery and may be combined with a micro infusion pump for maximum results in severe organ failure cases.

Also, it can produce the device may also be used for organ enhancement instead of just organ repair such as brain function enhancement.

The version of the system discussed for this Example includes the following components: 1. Micro bioelectric signal generator; 2. Programming wand; 3. Programming computer; 4. Pacing infusion lead; 5. Micro infusion pump; 6. PDGF bioelectric signal program; 7. PDGF solution; 8. Organ reading device and processor; 9. Organ reading software program and analysis software; and 10. Wireless energy beam transmitter.

Relationship Between the Components:

The (1) micro bioelectric stimulator is programmed with the (2) programming wand connected to the (3) programming computer with the (6) PDGF bioelectric signal of 20V 50 HZ 0.2 amps. The (1) micro stimulator is connected to the (4) pacing infusion lead and the other side of that lead is affixed in the central portion of the damaged or diseased target organ. The (2) programming wand connected to the (3) programming computer can active the (1) micro bioelectric stimulator to become an (8) organ reading device. When programmed with the (9) organ reading and analysis software the organ reader is able to read all the bioelectric activity of the failing organ as well as its phenotype, genotype including genetic defects and variation and chemical and biologically metabolism.

The bioelectric stimulation controlled PDGF expression causing new blood vessels to grow into the failing organ(s) and new healthy organ tissue to form. The reader adjusts the therapeutic dose as needed. The micro infusion pump refilled daily with a mixed stem cell based composition that includes PDGF and may also include SDF-1, IGF, EGF, HGF, HGH, Activin A+B, eNOS, VEGF, Follistatin, Tropoelastin. GDF-10, GDF-11 and Neurogenin-3, selected alkaloids, and selected anti-inflammatory factors may be used to supplement the bioelectric stimulation therapy for organ repair in seriously failing organs.

If the organ failure is severe, an added programmable, implantable, re-fillable micro infusion pump may be added to the therapy. The micro pump is refiled daily with about 2 ml of stem cell-based organ regeneration composition that includes PDGF. If it is not easy or desirable to reach the organ to be treated with a wire-based pacing infusion lead the operator a utilized the (10) wireless energy beam transmitter to deliver the bioelectric regeneration signals wirelessly to the organ.

In this embodiment, the stimulator, lead and programmer are essential. The micro infusion pump and mixed organ regeneration composition are optional.

The micro stimulator, and if chosen, the micro infusion pump are implanted somewhere below the skin of the patient with the pump silicone septum ports accessible for re-filling just below the skin. The stimulator must be in a location reachable by the programming wand attached to a portable computer. The pacing infusion lead form the stimulator+ pump is directed to the central damaged portion of the damaged organ i.e.; heart, kidney, pancreas, liver. The micro stimulator may optionally be non-invasive and external and can deliver its signal to the failing organ via a focalized wireless energy beam. Much like how they focalize radiation to treat cancer tumors, but this energy stimulates organ regeneration.

Additionally: The micro stimulator may be programmed with additional protein expressions. The micro pump may be used a stand-alone device. The sequence of use may be changed.

Also, it can create: The device may also be used for organ enhancement instead of just organ repair such as brain function enhancement.

Two PDGF expression control signals. One low voltage and one higher voltage. Test tissue was sheep heart tissue. Test cells were mesenchymal stem cells. 30% PDGF increase with 3 V/cm, 10 Hz, µA (0.000002 amps) and pulse duration of 0.2 ms. 230% PDGF increase with 20 V/cm 100 Hz, 0.25 µA (2.5e-7 amps) and pulse duration of 40 pulses/s, width of 100 µs.

Example—Treating Cancer Tumors Using Bioelectric Stimulation in Combination with Micro Infusion Previous cancer treatments failed to address the combination of stopping cell proliferation and blood supply followed by regenerating the damaged tissue or organ.

Cytokine+Chemotherapeutic and regenerative treatment for certain cancers may be combined with low intensity, intermediate frequency alternating electric fields that are tuned to release specific beneficial proteins at specific time intervals. More specifically, cell proliferation inhibition and halting blood supply to tumors in the first treatment stage. The bioelectric stimulation treatment may be increased in volume and efficacy by the combination use of an implantable, programmable, re-fillable micro infusion pump that delivers anti-cell proliferation and anti-blood vessel growth proteins as well, if desired, standard cancer treatment drugs such as chemo therapy agents. The second stage of treatment is focused regeneration of cancer damaged tissues back to their most optimal healthy state. The regenerative phase comprises a sequence of recruiting reparative stem cells to the damaged organ by bioelectrically stimulating the release of SDF-1 (stem cell homing factor), followed by a controlled proliferation signal, a controlled blood vessel supply signal (VEGF) and if desired and useful release of Follistatin, tropoelastin, Hepatocyte Growth Factor, IGF-1 and Activin. The stimulation cycle causing release of beneficial proteins for regeneration may be upgraded in volume and speed of delivery by the combination use of an implantable, re-fillable, programmable micro infusion pump for delivering a higher quantity of stem cells, nutrient hydrogel, matrix and beneficial tissue and organ regeneration promotion proteins.

Cytokine+Chemotherapeutic and regenerative treatment for certain cancers comprising a combination low intensity, intermediate frequency alternating electric fields that are tuned to release particular beneficial proteins in two stages, stage (1)=stopping cancer spread by halting cell proliferation and halting tumor blood supply and stage (2) regenerating the cancer damaged tissue or organ back to optimal health. In many cases, the resulting cell proliferation inhibition is significantly higher than the inhibition obtained by drug-only regimens of treatment.

A method of killing or inhibiting the growth of cancer cells in a target region followed by regenerating the tissue or organ back to optimal health, the method comprising the steps of:

Stage 1=Stop cancer growth applying, to the target region, a series of bioelectric signals that damages the cancer cells or inhibits the growth of the cancer cells via stopping cell proliferation and halting blood supply temporarily, but leaves normal cells in the target region substantially unharmed; and treating the cancer cells with another anti-cancer regimen via programmable micro pump infusion, wherein the applying step and the treating step are performed simultaneously.

Stage 2=Regeneration of post cancer tissue or organ treating the target region with a series of bioelectric signals to recruit stem cells, grow healthy blood vessels and re-grow healthy functional tissues in the previous cancer damaged region In such a method, in the applying step, the field may be applied in at least two different directions in an alternating sequence to halt cell proliferation and to stop blood supply to the tumor.

In such a method, the other anti-cancer regimen may comprise treating the cancer cells with an anti-cancer drug. In this method, the drug may comprise at least one drug selected from the group consisting of paclitaxel, doxorubicin cyclophosphamide, and cisplatin. In such a case, the drug dosage may be less than 20% of a standard dosage for the drug.

In such a method, the bioelectric stimulation may release any one of these regeneration of tissue and organ beneficial proteins SDF-1, IGF-1, Activin, HGF, VEGF, Follistatin or tropoelastin and in specific sequences for optimal organ health.

In such a method, all bioelectric regeneration signal may be delivered wirelessly and/or non-invasively.

In such a method, the target cancer may be breast cancer and the target regenerative organ may be breast reconstruction.

In such a method, the target cancer may be brain cancer and the target regenerative organ is brain.

In such a method, the target cancer may be prostate cancer and the target regenerative organ may be the prostate.

In such a method, the target cancer may be colon cancer and the target regenerative organ may be the colon.

In such a method, the target cancer may be throat or esophageal cancer and the target regenerative organ may be throat or esophagus.

In such a method, the target cancer may be pancreas cancer and the target regenerative organ may be the pancreas with improved insulin production.

In such a method, the target cancer may be lung cancer and the target regenerative organ may be lung(s).

In such a method, the target cancer may be eye cancer and the target regenerative organ may be the eye.

Example

A combination protein expression stimulator, micro infusion pump, and fifteen (15) component stem cell-based composition for saving brain function in a subject following stroke or injury.

Brain function is lost when a stroke or brain injury occurs in a subject due to lack of oxygen and nutrients reaching a particular portion of the brain. Prior art therapies are typically drugs that do nothing to regenerate lost brain tissue. Chemical drugs do not do anything to affect neurogenesis (the growth of new brain tissue to replace damaged brain tissue). For example, the most popular simply dissolves blood clots, stopping further damage, but doing nothing to recover brain tissue already lost.

Prior art electrical stimulation devices do not have the correct signals for homing stem cells or for regenerating brain tissue. Existing electrical stimulation devices deliver one signal and that signal does not promote regeneration of lost brain tissue. Burst electrical pulses of old-type stimulators do nothing to affect neurogenesis.

Prior art one-time stem cell injections of one type of stem cell or modified stem cell have achieved some success, but this therapy is limited and incomplete. One-time needle injection cell therapies are too limited to recover major lost brain function. One-time injection of stem cells on a stand-alone basis mostly die out without a support system and cannot affect major neurogenesis.

The herein described combination of bioelectric stimulation of ten (10) key regeneration proteins via bioelectric signals, 24 hours a day for seven days a week, combined with daily or weekly infusions of the herein described fifteen component compositions provides much more complete repair, recovery, and regeneration of lost brain function.

The herein described device, method, and system practice all forms of "good farming" to grow a "new crop" of functional brain tissue in the skulls of post-stroke and post-injury subjects.

The herein described system rapidly and easily delivers ten (10) brain regeneration promoting bioelectric signals to the subject within minutes, combined with a micro infusion pump that delivers fifteen (15) component angiogenic and regeneration compositions rapidly and safely. This, in combination, can fully restore brain functionality back to normal.

The ten (10) key regeneration proteins are SDF-1 (stem cell homing signal), IGF-(1 DNA repair and brain regeneration signal), HGF, EGF, Activin A+B, eNOS, VEGF, follistatin, and tropoelastin signal as described herein.

The system discussed in this Example preferably includes: the bioelectric signal generator, a programmable, re-fillable micro infusion pump, a brain saving helmet with electroacupuncture needles built in (but see below), micro infusion leads stereotaxic directed to deep brain regions, a fifteen component angiogenic composition, a fifteen component regeneration composition, human placenta, fetal serum, a cell proliferation signal, and a cell controlled differentiation signal.

In use, the bioelectric signal generator and the micro infusion pump are both attached to the brain saving helmet with electroacupuncture needles (not shown). The helmet is placed on the head of the patient. If the brain saving helmet with electroacupuncture needles is not used, one may use "off the shelf" standard, readily available electro-acupuncture needles. The bioelectric signal generator stimulator is activated and the micro infusion pump is filled with first the fifteen component angiogenic composition to increase blood flow and then the next day with the fifteen component regeneration composition.

The bioelectric stimulator cycles through the SDF-1 signal for stem cell homing, then IGF-1 for DNA repair, then HGF, EGF, Activin A+B, eNOS, VEGF, follistatin, tropoelastin, cell proliferation, and cell differentiation. The micro infusion pump may be re-loaded with fetal serum and placenta in severe cases to enhance results. Anti-inflammatory agents may also be used. The bioelectric signal generator stimulator recruits stem cells, causes release of regeneration support factors, and multiples cells, and then controls their differentiation into healthy full functioning brain tissue.

The micro infusion pump is filled daily or week with the fifteen component angiogenic and regeneration compositions designed to facilitate neurogenesis. The fifteen component angiogenic and regenerative compositions provide much more complete repair, recovery, and regeneration of lost brain function.

If electrical stimulation alone does not work, the micro pump is filled with angiogenic and regeneration compositions for daily delivery. If those compositions do not work, then fetal serum and placenta may be added.

A bioelectric signal generator can be as described otherwise herein. For some signals, a drop down resistor in the pacing infusion lead may be necessary to drop the lowest voltage and current from the standard pacemakers down to a natural micro voltage level (the same level of natural electricity in a human body). A micro infusion pump can be as described otherwise herein and may be sourced from various drug delivery pump manufacturers and adapted by taking any filters out. The compositions for angiogenic and regeneration purposes are comprised of mixing together components that can be obtained from a person's own body as described herein further processed in a standard cell culturing laboratory (many contract manufacturers are available) or from reliable known suppliers.

The bioelectric signal generator is essential. All other components may be optional. The micro infusion pump, compositions, fetal serum, placenta, and anti-inflammatory agents are only necessary if the bioelectric stimulation on its own has not restored complete function or (e.g., in emergency recovery cases) where time is of the essence such as in an acute stroke situation.

One could use the compositions on their own injected by needle syringe. One could use the micro infusion pump on its own filled with other mixes of stem cells or drugs. One could use the bioelectric stimulator on its own running only one or a few signal programs instead of all of them, or one could program the bioelectric stimulator for entirely different signaling.

Upon arrival to the location of an acute stroke patient, a rapid assessment is made including video phone examination of the patient. A clot dissolving drug is first administered. Then, the brain-saving helmet is placed on the patient's head, and the bioelectric signal generator is turned on running though all ten (10) regeneration signals and the micro infusion pump is loaded first with an angiogenic composition followed immediately thereafter with a regeneration composition. If normal brain function is not restored in the subject with the above steps, the micro infusion pump may be re-filled with fetal serum, placenta, and anti-inflammatory agents, which are then administered.

The herein described system can produce/may be adapted to regenerate other organs including: skin, face, aorta, heart, eyes, arteries, joints, heart valves, limbs, lungs, kidneys, pancreas, liver, bladder, whole body, biological pacemaker, and breasts, and to treat erectile dysfunction, COPD, snoring and incontinence.

REFERENCES (The contents of the entirety of each of which is incorporated herein by this reference.)

Thattaliyath et al. "Modified Skeletal Myoblast Therapy For Cardiac Failure Using AAV SDF1,"*Proc. Intl. Soc. Mag. Reson. Med.* 16, page 579 (2008).

Prochazka et al. "Cocktail of Factors from Fat-derived Stem Cells Shows Promise for Critical Limb Ischemia" http://www.sciencenewsline.com/news/2016012204520017.html (Jan. 21, 2016).

Wei et al. "Epicardial FSTL1 reconstitution regenerates the adult mammalian heart,"*Nature* 525: 479-485 (24 Sep. 2015).

"Hearts build new muscle with this simple protein patch," jacobsschool.ucsd.edu/news/news_releases/release.sfe?id=1813 (Sep. 16, 2015).

Stenn et al. "Bioengineering the Hair Follicle,"*Organogenesis,* 3(1): 6-13 (January-March 2007).

Salcedo et al. "Low current electrical stimulation upregulates cytokine expression in the anal sphincter,"*Int. J. Colorectal Dis.,* 2012 February; 27 (2):221-5. doi: 10.1007/s00384-011-1324-3. Epub (October 2011).

Marie Ellis "Cure for baldness? Stem cells bring hope" http://www.medicalnewstoday.com/articles/271898.php.

Alice Park "Shrinking Stem Cells Are the Real Reason for Hair Loss"*Time*, (Feb. 5, 2016).

Robert Ferris "Battle against baldness turns to stem cells" http://www.cnbc.com/2015/01/29/studies-indicate-itspossible-to-use-stem-cells-to-cure-baldness.html (Jan. 29, 2015).

"Control of pelage hair follicle development and cycling by complex interactions between follistatin and activin, "*FASEB J.* (Jan. 2, 2003).

Chen et al. "Regenerative Hair Waves in Aging Mice and Extra-Follicular Modulators Follistatin, Dkk1, and Sfrp4, "*Journal of Investigative Dermatology*, August 2014, Volume 134, Issue 8, Pages 2086-2096.

Li et al. "Exogenous IGF-1 promotes hair growth by stimulating cell proliferation and down regulating TGF-β1 in C57BL/6 mice in vico,"*Growth Hormone & IGF Research*, Volume 24, Issues 2-3, Pages 89-94 (April-June 2014).

"Our Approach to Improve Hair Loss by Increasing Hair Growth Factor IGF-1," http://www.jhgc.com.sg/theory/igf-1/index.html.

Hy et al. "Insulin-like growth factor 1 and hair growth, "*Dermatol. Online J.;* 5(2):1 (November 1999).

Lee et al. "Hepatocyte growth factor (HGF) activator expressed in hair follicles is involved in in vitro HGF-dependent hair follicle elongation,"*J. Dermatol. Sci.,* 25 (2):156-63 (February 2001).

Fukuoka and Suga, "Hair Regeneration Treatment Using Adipose-Derived Stem Cell Conditioned Medium: Follow-up With Trichograms," *Eplasty,* 15:e10 (March 2015).

Fukuoka et al. "The Latest Advance in Hair Regeneration Therapy Using Proteins Secreted by Adipose-Derived Stem Cells,"*The American Journal of Cosmetic Surgery,* 29 (4):273-282 (2012).

"Reversing Age-Related Hair Loss and Restoring Healthy Hair Growth in Men and Women" https://nutritionreview.org/2015/08/reversing-age-related-hair-loss-and-restoring-healthy-hair-growth-in-men-and-women/ (Aug. 24, 2015).

Yamakazi et al. "Hair cycle-dependent expression of hepatocyte growth factor (HGF) activator, other proteinases, and proteinase inhibitors correlates with the expression of HGF in rat hair follicles,"*J. Investig. Dermatol. Symp. Proc.,* 4 (3):312-5 (December 1999).

"Involvement of hepatocyte growth factor/scatter factor and Met receptor signaling in hair follicle morphogenesis and cycling," *FASEB J.*, February 2000 14:319 332.

"Interesting study about prolactin, VEGF and angiogenic inhibition," http://www.regrowth.com/hair/loss-forums/topic/interesting-study-about-prolactin-vegf-and-angiogenic-inhibition/ (November 2006).

"Control of Hair Growth by a Growth Factor Protein," http://www hairloss-reversible.com/control-of-hair-growth-by-a-growth-factor-protein/.

"Hair Growth Factors," Nanogen, http://www.svijet-kose.com/dokumenti/Serum-vegf.pdf.

"Blood Vessels Hold Key To Thicker Hair Growth," https://www.sciencedaily.com/releases/2001/02/010215074636.htm (February 2001).

Jia et al. "Activin B Promotes Initiation and Development of Hair Follicles in Mice,"*Cells Tissues Organs,* 198:318-326 (February 2014).

"Elastatropin® in Scalp & Hair Conditioning," https://www.proteingenomics.com/haircare.html.

"What Is Elastin?" http://www.keracyte.com/index.php/site/page?view=whatIsElastin Park et al. "Effects of SM-215 on Hair Growth by Hair Follicle Stimulation," *Indian Journal of Science and Technology*, Vol 8 (25), DOI: 10.17485/ijst/2015/v8i25/80263, (October 2015).

Thattaliyath et al. "Modified Skeletal Myoblast Therapy For Cardiac Failure Using AAV SDF1,"*Proc. Intl. Soc. Mag. Reson. Med.* 16, p. 579 (2008).

"Electrical brain stimulation could support stroke recovery," https://www.sciencedaily.com/releases/2016/03/160316151108.htm (Mar. 16, 2016).

"Electric Tumor Treatment Fields," No. 0827 Policy, http://www.aetna.com/cpb/medical/data/800_899/0827.html (Nov. 18, 2016).

D. Grady "Electrical Scalp Device Can Slow Progression of Deadly Brain Tumors,"*New York Times*, https://www.nytimes.com/2014/11/16/health/electrical-scalp-device-can-slow-progression-of-deadly-brain-tumors.html?_r=0 (Nov. 15, 2014).

B. Borgobello "FDA approves the treatment of brain tumors with electrical fields,"*New Atlas*, http://newatlas.com/treatment-of-brain-tumors-with-electrical-fields/21433/ (Feb. 13, 2012).

Hopkins Medicine "Overview of Pacemakers and Implantable Cardioverter Defibrillators (ICDs)," http://www.hopkinsmedicine.org/healthlibrary/conditions/cardiovascular_diseases/overview_of_pacemakers_and_implantable_cardioverter_defibrillators_icds_85,P00234/.

Medtronic "Cardiac Resynchronization Therapy (CRT) Devices For Heart Failure," http://www.medtronic.com/us-en/patients/treatments-therapies/crt-devices.html.

Columbia "Implant Procedure Concepts-Pacemaker, ICD and CRT Overview," http://www.columbia.edu/itc/hs/medical/hickey/docs/Pacemaker.%20ICD%20and%20CRT%20Overview%20022007.pdf "FDA Approves Algovita Spinal Cord Stimulation System from Greatbatch," http://www.odtmag.com/contents/view_breaking-news/2015-12-02/fda-approves-algovita-spinal-cord-stimulation-system-from-greatbatch (Dec. 2, 2015).

Mass Device "Greatbatch wins FDA PMA for Algovita SCS," http://www.massdevice.com/greatbatch-wins-fda-pma-for-algovita-scs/ (Dec. 1, 2015).

P. Banerjee "Electrical muscle stimulation for chronic heart failure: an alternative tool for exercise training?"*Curr. Heart Fail. Rep.,* 7(2):52-8. doi: 10.1007/s11897-010-0013-9 (June 2010).

HN Sabbah "Electrical vagus nerve stimulation for the treatment of chronic heart failure,"*Cleve. Clin. J. Med.,* 78 Suppl. 1:S24-9. doi: 10.3949/ccjm.78.s1.04 (August 2011).

Bio-Leonhardt "Micro Stimulator" http://www.bioleonhardt.com/micro-stimulator/.

HU Klein "Vagus Nerve Stimulation: A new approach to reduce heart failure"*Cardiology Journal* (2010).

"Israeli innovation uses nerve stimulation to treat heart failure" https://www.israel21c.org/israeli-innovation-uses-nerve-stimulation-to-treat-heart-failure/ (Feb. 11, 2007).

Sahoo and Losordo "Exosomes and Cardiac Repair After Myocardial Infarction,"*Circulation Research,* 114:333-344 (Jan. 16, 2014).

Tamaki et al. "Cardiomyocyte Formation by Skeletal Muscle-Derived Multi-Myogenic Stem Cells after Transplantation into Infarcted Myocardium,"*PLoS ONE* 3(3): e1789. doi:10.1371/journal.pone.0001789 (March 2008).

W. Hoffmann "Regeneration of the gastric mucosa and its glands from stem cells,"*Curr. Med. Chem,* 15 (29):3133-44 (2008).

What is claimed is:

1. A system for stimulating a target tissue in a subject, the system comprising:
    a bioelectric stimulator programmed to produce bioelectric signals that stimulate the target tissue to express and/or release stromal cell-derived factor 1 ("SDF-1") and platelet-derived growth factor ("PDGF"),
      wherein the bioelectric signal to produce SDF-1 comprises:
        30 pulses per second with a voltage of 3.5 mV, and successively alternating currents of 700 to 1500 picoamps for one minute, and again with 700 to 1500 picoamps for one minute, plus stimulated with a current of 0.25 mA, pulse duration of 40 pulses per second, pulse width of 100 μs, and frequency of 100 Hz, each signal for 40 minutes to 8 hours a day, and
      wherein the bioelectric signal to produce PDGF comprises:
        3 V/cm, 10 Hz, 2 μA (0.000002 amps), and pulse duration of 0.2 ms, or 20 V/cm, 100 Hz, 0.25 μA (2.5e-7 amps), and pulse duration of 40 pulses/s, width of 100 μs; and
    a microinfusion pump for continuous or repeat delivery of a liquid composition to the target tissue.

2. The system of claim 1, wherein the microinfusion pump is programmable.

3. The system of claim 1, wherein the microinfusion pump is re-fillable with low cell damage to the subject.

4. The system of claim 3, wherein the microinfusion pump includes silicon septum ports and associated reservoir chambers for the liquid composition.

5. The system of claim 1, wherein the microinfusion pump comprises a refilling silicon septum port and reservoir chamber for the liquid composition.

6. The system of claim 5, wherein the liquid composition further comprises muscle-derived stem cells.

7. The system of claim 1, wherein the liquid composition comprises adipose-derived stem cells, exosomes, MicroRNAs, nutrient hydrogel, growth factor cocktail, alkaloids, and an anti-inflammatory agent.

8. A method of using the system of claim 1 to stimulate tissue of a subject, the method comprising:
    connecting the bioelectric stimulator and microinfusion pump to the target tissue and providing stimulation to the target tissue.

9. The method of claim 8, wherein the connection is via conductive soft wrap.

10. The system of claim 1, wherein the bioelectric stimulator is further programmed to produce a bioelectric signal of 200 picoamps for 10 seconds for one (1) hour with a pulse having an amplitude of 5 volts and a width of 0.5 milliseconds for one (1) hour.

11. The system of claim 1, wherein the microinfusion pump is configured for repeat delivery of the liquid composition to the target tissue.

12. A system for stimulating a target tissue in a subject, the system comprising:
    a bioelectric stimulator programmed to produce bioelectric signals that stimulate the target tissue to express and/or release stromal cell-derived factor 1 ("SDF-1") and platelet-derived growth factor ("PDGF"),
      wherein the bioelectric signal to produce SDF-1 comprises:
        30 pulses per second with a voltage of 3.5 mV, and successively alternating currents of 700 to 1500 picoamps for one minute, and again with 700 to 1500 picoamps for one minute, plus stimulated with a current of 0.25 mA, pulse duration of 40 pulses per second, pulse width of 100 μs, and frequency of 100 Hz, each signal for 40 minutes to 8 hours a day, and
      wherein the bioelectric stimulator is further programmed to produce a bioelectric signal of 10V at 50 HZ and 100 Hz, 0.25 mA for one (1) minute; and
    a microinfusion pump for continuous or repeat delivery of a liquid composition to the target tissue.

13. A system for stimulating a target tissue in a subject, the system comprising:
    a bioelectric stimulator programmed to produce bioelectric signals that stimulate the target tissue to express and/or release stromal cell-derived factor 1 ("SDF-1") and platelet-derived growth factor ("PDGF"),
      wherein the bioelectric signal to produce SDF-1 comprises:
        30 pulses ver second with a voltage of 3.5 mV, and successively alternating currents of 700 to 1500 picoamps for one minute, and again with 700 to 1500 picoamps for one minute, plus stimulated with a current of 0.25 mA, pulse duration of 40 pulses per second, pulse width of 100 s, and frequency of 100 Hz, each signal for 40 minutes to 8 hours a day, and
      wherein the bioelectric stimulator is further programmed to produce a bioelectric signal of 0.06 V with 50 Hz alternating electrical field and electric current of 1 mA for 15 minutes and 3 mA for 15 minutes; and
    a microinfusion pump for continuous or repeat delivery of a liquid composition to the target tissue.

14. A system for stimulating a target tissue in a subject, the system comprising:
    a bioelectric stimulator programmed to produce bioelectric signals that stimulate the target tissue to express and/or release stromal cell-derived factor 1 ("SDF-1") and platelet-derived growth factor ("PDGF"),
      wherein the bioelectric signal to produce SDF-1 comprises:

30 pulses ver second with a voltage of 3.5 mV, and successively alternating currents of 700 to 1500 picoamps for one minute, and again with 700 to 1500 picoamps for one minute, plus stimulated with a current of 0.25 mA, pulse duration of 40 pulses per second, pulse width of 100 μs, and frequency of 100 Hz, each signal for 40 minutes to 8 hours a day, and wherein the bioelectric stimulator is further programmed to produce a bioelectric signal applied to the target tissue of 3 mV with electric frequency of 22 Hz, and current of 1 mA for 15 minutes and 3 mA for 15 minutes; and a microinfusion pump for continuous or repeat delivery of a liquid composition to the target tissue.

* * * * *